United States Patent
Peyvan

(10) Patent No.: US 9,308,508 B2
(45) Date of Patent: Apr. 12, 2016

(54) SEQUENTIAL DELIVERY DEVICE AND METHOD

(71) Applicant: Kianoosh Peyvan, Seattle, WA (US)

(72) Inventor: Kianoosh Peyvan, Seattle, WA (US)

(*) Notice: Subject to any disclaimer, the term of this patent is extended or adjusted under 35 U.S.C. 154(b) by 0 days.

(21) Appl. No.: 14/335,946

(22) Filed: Jul. 21, 2014

(65) Prior Publication Data

US 2015/0024384 A1 Jan. 22, 2015

Related U.S. Application Data

(60) Provisional application No. 61/857,137, filed on Jul. 22, 2013.

(51) Int. Cl.
*B01J 4/02* (2006.01)
*B01L 3/00* (2006.01)
*B01F 15/02* (2006.01)
*C12N 15/10* (2006.01)

(52) U.S. Cl.
CPC ............ *B01J 4/02* (2013.01); *B01F 15/0206* (2013.01); *B01F 15/0223* (2013.01); *B01F 15/0224* (2013.01); *B01F 15/0233* (2013.01); *B01L 3/527* (2013.01); *B01F 2015/0221* (2013.01); *B01J 2219/00177* (2013.01); *B01L 2300/0672* (2013.01); *B01L 2300/087* (2013.01); *B01L 2400/0409* (2013.01); *B01L 2400/049* (2013.01); *C12N 15/1003* (2013.01)

(58) Field of Classification Search
CPC .. B65D 81/3211; B65D 81/3233; B01L 3/52; B01L 3/527; B01L 2300/0672
See application file for complete search history.

(56) References Cited

U.S. PATENT DOCUMENTS

| | | | |
|---|---|---|---|
| 2,932,385 A | 4/1960 | Vokaty et al. | |
| 3,036,894 A | 5/1962 | Forestiere | |
| 3,713,779 A | 1/1973 | Sirago et al. | |
| 4,458,811 A | 7/1984 | Wilkinson | |
| 4,515,753 A | 5/1985 | Smith et al. | |
| 4,770,853 A * | 9/1988 | Bernstein | 422/413 |
| 4,916,078 A | 4/1990 | Klose et al. | |
| 4,971,765 A | 11/1990 | Loretti et al. | |
| 5,058,770 A * | 10/1991 | Herold et al. | 222/80 |
| 5,273,718 A * | 12/1993 | Skold et al. | 422/553 |
| 5,288,463 A | 2/1994 | Chemelli | |
| 5,290,518 A | 3/1994 | Johnson | |

(Continued)

FOREIGN PATENT DOCUMENTS

EP 0925113 B1 9/1997
EP 2233210 A1 9/2010

*Primary Examiner* — Jill Warden
*Assistant Examiner* — Matthew Krcha
(74) *Attorney, Agent, or Firm* — Nima Seyedali

(57) ABSTRACT

A reagent delivery device includes a reagent delivery column with a housing receiving reagent storage elements that can move, and a breaching element coupled to the housing. The device includes an actuation member that during operation forces the reagent storage elements toward the breaching element. Breaching the storage elements releases the reagent. The breaching element and/or the housing are configured to communicate reagent between the reagent storage element and a target chamber coupled to the housing. The breaching element can be a needle, a blade, or a combination thereof. Multiple reagent delivery columns can be coupled to microplate wells for larger scale reagent delivery and processing. Biasing elements such as a spring and a counterweight can be directly or indirectly coupled to the housing and/or the reagent storage elements, resisting and/or moderating movement of the reagent elements.

13 Claims, 21 Drawing Sheets

(56) References Cited

U.S. PATENT DOCUMENTS

| | | |
|---|---|---|
| 5,599,660 A | 2/1997 | Ramanujam et al. |
| 5,601,711 A | 2/1997 | Sklar et al. |
| 5,639,428 A | 6/1997 | Cottingham |
| 5,865,799 A | 2/1999 | Tanaka et al. |
| 5,879,635 A | 3/1999 | Nason |
| 6,015,880 A | 1/2000 | Baldeschwieler et al. |
| 6,048,735 A | 4/2000 | Hessel et al. |
| 6,153,148 A | 11/2000 | Thomas |
| 6,221,655 B1 | 4/2001 | Fung et al. |
| 6,302,134 B1 | 10/2001 | Kellogg et al. |
| 6,399,361 B2 | 6/2002 | Brotherston et al. |
| 6,419,656 B1 | 7/2002 | Vetter et al. |
| 6,488,894 B1 | 12/2002 | Miethe et al. |
| 6,527,432 B2 | 3/2003 | Kellogg et al. |
| 6,911,181 B1 * | 6/2005 | McNeil .................. 422/505 |
| 7,273,702 B2 | 9/2007 | Akashi et al. |
| 7,323,660 B2 | 1/2008 | Bedlingham et al. |
| 7,749,388 B2 | 7/2010 | Pai et al. |
| 8,003,926 B2 | 8/2011 | Bedlingham et al. |
| 8,329,119 B2 | 12/2012 | Pearcy et al. |
| 8,652,422 B2 | 2/2014 | Mabuchi et al. |
| 2003/0039588 A1 | 2/2003 | Miethe et al. |
| 2003/0205097 A1 * | 11/2003 | Wickstead et al. ......... 73/863.32 |
| 2004/0156915 A1 * | 8/2004 | Harman et al. ............... 424/600 |
| 2004/0209266 A1 | 10/2004 | Squirrell |
| 2010/0300559 A1 | 12/2010 | Schultz et al. |
| 2011/0127294 A1 | 6/2011 | Pearcy et al. |
| 2012/0073667 A1 | 3/2012 | Schultz et al. |
| 2012/0107811 A1 | 5/2012 | Kelso et al. |
| 2013/0109082 A1 | 5/2013 | Quinn et al. |

* cited by examiner

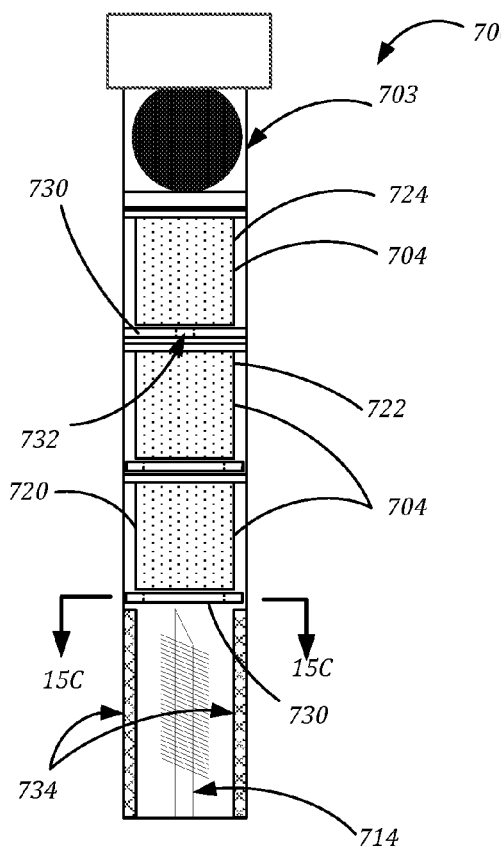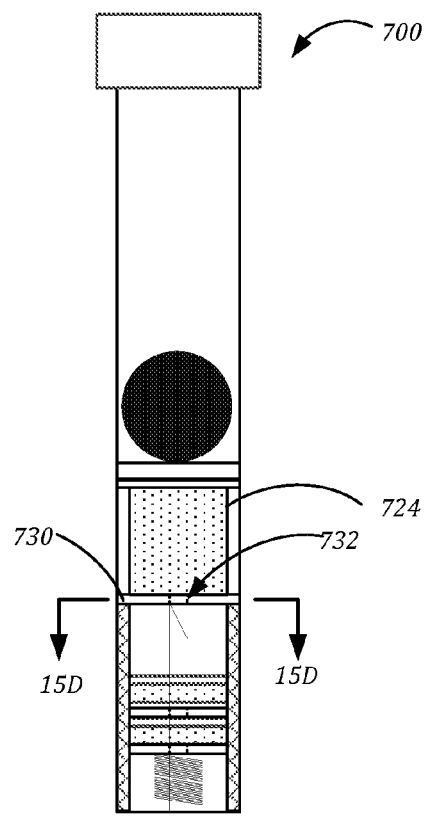
FIG. 15A　　　　　　　FIG. 15B
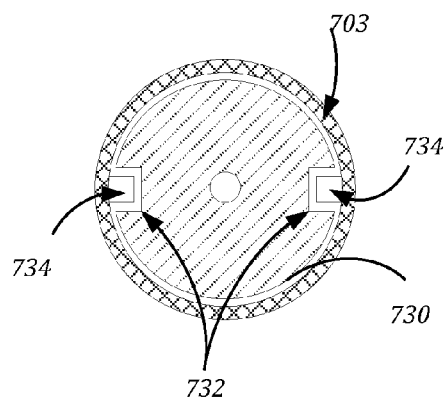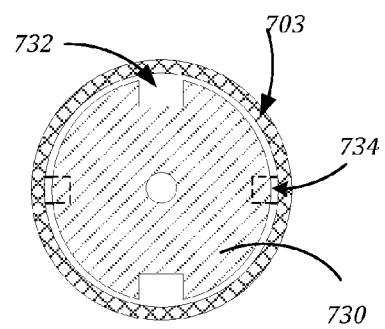
FIG. 15C　　　　　　　FIG. 15D

SEQUENTIAL DELIVERY DEVICE AND METHOD

BACKGROUND

1. Technical Field

The present disclosure relates to the field of reagent delivery, and more particularly, to devices and methods delivering reagents in an automated and sequential manner.

2. Description of the Related Art

Various chemical, biological, or other applications can benefit from automated fluidic or reagent delivery. Examples include, and are not limited to RNA, DNA, protein extraction and purification from biological samples, hybridization of nucleic acid to microarrays, immunological assays, protein and western blots processing, or more generally separation of a chemical which requires incubation of a set of known reagent.

These processes are typically performed in well-equipped laboratories. They generally involve delivery of various reagents onto a target chamber which often times is the core or contains the active component for that process. For example, extraction of nucleic acid includes using an active component, which is the matrix inside a "spin column." In microarray based hybridization the active component is an array of capture probes. These reagents can play many roles such as buffering or changing the PH of the core chamber contents or changing its salt concentration. In addition, or instead, they can act as washes, or be the solution in which the target of interest is dissolved. It is desirable these reagents be prepared, procured, mixed, and/or stored in sanitary environments and conditions, and delivered in accurate amounts to the process core in a predefined sequence and/or timing.

One such process example, SPE or solid phase extraction, is a separation process by which compounds, dissolved or suspended in fluid mixture, are separated from other compounds in the mixture according to their physical and chemical properties. Analytical laboratories use solid phase extraction to concentrate and/or purify samples for analysis.

For example, solid phase extraction can be used to isolate analytes of interest from a wide variety of sources, including, but not limited to, urine, blood, water, beverages, soil, and animal tissue. SPE uses the affinity of solutes dissolved or suspended in a liquid (known as the mobile phase) for a solid through which the sample is passed (known as the stationary phase) to separate a mixture into desired and undesired components. The result is that either the desired analytes of interest or undesired impurities in the sample are retained on the stationary phase. The portion that passes through the stationary phase is collected, transferred, or discarded, depending on whether it contains the desired analytes or undesired impurities. If the portion retained on the stationary phase includes the desired analytes, they can then be removed from the stationary phase for collection in an additional step, in which the stationary phase is rinsed with an appropriate eluent.

Existing devices and methods used to facilitate reagent delivery for various steps of aforementioned or other existing processes are generally time consuming, inefficient, and prone to operator error and environmental contaminants, and have cost drawbacks. For example, the classic manual pipetting of reagents is time-consuming, resource dependent, and expensive. Manual pipetting requires multiple manually performed steps of dispensing solutions such as suspensions and washing buffers, consuming scientist labor and requiring numerous tools and consumables such as multiple pipettes, pipette tips and vials. Other manually operated devices that attempt to improve on manual pipetting, continue to consume scientist labor and time, and are limited in application.

Two significant drawbacks of manual operation is operator error and environmental contaminants. Automatic pipetting similarly requires exceedingly expensive equipment. Certain existing automated or semi-automated devices are either intended for solely microfluidic applications or are otherwise extremely complicated and expensive to manufacture, purchase, and operate. Some automated devices require complicated internal mechanisms and/or requirements, which make it extremely difficult to load reagents.

An additional drawback of some existing devices includes the lack of capability to assemble, organize, or arrange reagents separate from the devices, and requiring the devices to serve as the reagent container.

By way of a particular example, the following is an existing RNA extraction procedure based on existing Qiagen™ RNeasy Mini Spin Columns™.

The RNeasy™ kit provides protocols and reagents for purification of total RNA from animal cells, animal tissues, plant cells and tissues, filamentous fungi and yeast, and for cleanup of RNA from crude RNA preps and enzymatic reactions (e.g., DNase digestion, proteinase digestion, RNA ligation, and labeling reaction).

The RNeasy™ Mini Kit can also be used to purify total RNA from bacteria. The purified RNA is suitable for downstream applications such as:

RT-PCR and real-time RT-PCR
Differential display
cDNA synthesis
Northern, southern, and western, dot, and slot blot analyses
Primer extension
Poly A+RNA selection
RNase/S1 nuclease protection
Microarrays.

Summarized Protocol:

1) Sample preparation:

Disrupt the sample according to the appropriate protocol in order to release RNA into solution. Most often, the solution is RLT lysis buffer. Add one volume of 70% ethanol to the lysis buffer and mix.

2) Binding.

Add up to 700 µl of solution (RLT+EtOH+sample) to the Qiagen™ spin column, close the lid, and centrifuge at ≥8000 rcf for 15 seconds.

3) Washes:

Remove the column from the collection tube, empty the flow-through, and return the column back to the collection tube. Add 700 µl RW1 wash buffer to the column, close the lid, and centrifuge at ≥8000 rcf for 15 seconds. Remove the column from the collection tube, empty the flow-through, and return the column back to the collection tube. Add 500 µl RPE (1:4 RPE concentrate to 100% EtOH, premixed) to the column, close the lid, centrifuge at ≥8000 rcf for 15 seconds. Remove the column from the collection tube, empty the flow-through, and return the column back to the collection tube. Repeat the RPE wash two more times. Dry the column by removing the column from the collection tube, wiping residual solution off of the column, putting the column into a clean collection tube, and centrifuging at ≥8000 rcf for 1 minute.

4) Elution:

Place the column into a new collection tube, add 30-50 µl of elution water, close the lid, and centrifuge at ≥8000 rcf for 15 seconds. The eluent will contain the RNA and is ready for downstream applications.

As demonstrated above, this is one example, which requires multiple steps, demanding scientist time and expensive components.

BRIEF SUMMARY

According to one embodiment, a reagent delivery device includes at least one reagent delivery column having a housing, the housing including a housing volume, reagent storage elements configured to store reagent and movably positioned in the housing volume, and a breaching element coupled to the housing and configured to breach the reagent storage elements, for example, sequentially. At least one of the breaching element and the housing are configured to communicate reagent from at least one of the reagent storage element and the housing volume, to an external volume located externally with respect to the housing volume.

In one aspect the reagent delivery device can include an actuation source configured to bias the reagent storage elements toward the breaching element.

In one aspect the actuation source includes a centrifugal device, a vacuum device, a threadedly actuated device, or a push device, or any combination thereof.

In one aspect the reagent storage elements include a plurality of reagent storage elements, at least a first group of the plurality of reagent storage elements storing an inert or buffer content and a second group thereof storing active reagent, the respective reagent storage elements of the first group being positioned between the respective reagent storage elements of the second group.

In one aspect the device includes a target chamber coupled to the reagent delivery column and forming the external volume in fluid communication with at least one of the breaching element and the housing volume.

In one aspect the target chamber includes a binding matrix, the target chamber having a first target chamber volume in fluid communication with the binding matrix, and adapted to receive reagent communicated through the binding matrix.

In one aspect the device further includes a second target chamber volume and a transfer manifold in fluid communication with the binding matrix and movably coupled with respect to the target chamber. The transfer manifold can be selectively moved between a first position in which it is adapted to communicate fluid between the binding matrix and the first volume, and a second position in which it is adapted to communicate fluid between the binding matrix and the second volume.

In one aspect the delivery column is removably coupled to the target chamber.

In one aspect the device includes at least one spacer element positioned between adjacent reagent storage elements.

In one aspect the device includes a control system configured to moderate movement of the reagent storage elements toward the breaching element.

In one aspect the control system includes a keyed spacer having a first key feature, and the housing includes a second key feature complementary to the first key feature. The keyed spacer can be selectively moved between a first orientation in which the first and second key features are misaligned, and a second orientation in which the first and second key features are aligned.

In one aspect the control system includes at least one of a counterweight and a biasing device, the biasing device positioned to at least partially resist movement of the reagent storage element toward the breaching element.

In one aspect the actuation source can include a centrifugal device configured to rotate and receive the reagent delivery column. The counterweight can be positioned adjacent a first side of the reagent storage elements distal with respect to the breaching element, the counterweight and the biasing device exerting respective forces in different, for example opposite, directions to the reagent storage elements.

In one aspect the breaching element includes at least one of a hollow needle, a solid blade, and a blade leading edge coupled to a hollow stem including a side having an orifice therethrough.

In one aspect the column can include a plug element coupled to the housing, and securing the breaching element. The plug element can include at least one peripheral opening therethrough to communicate reagent and/or prevent vacuum build up in the column.

In one aspect each reagent storage element is coupled to the adjacent storage element, the plurality of reagent storage elements forming a storage element stack.

In one aspect the reagent storage elements each include an assembly including a first reagent storage element and at least a second reagent storage element coupled to the first reagent storage element in close proximity to facilitate mixing of reagent contained in the first and second reagent storage elements in the housing volume upon the breaching element breaching the assembly. For example, the assembly can include one reagent storage element nested or housed in another reagent storage element, the two reagent storage elements containing different reagents.

According to one embodiment, a reagent delivery apparatus includes a plurality of reagent delivery columns each including a housing, a plurality of reagent storage elements having a reagent stored therein and received in the housing, and a breaching element configured to breach the reagent storage elements and release the reagent therein, at least one of the breaching element and the housing configured to communicate released reagent to a volume outside the housing, and a microplate having a plurality of wells, each reagent delivery column being in fluid communication with at least one well to communicate reagent thereto.

According to one embodiment, a method for delivering reagent includes forcing at least one reagent storage element containing a reagent toward a breaching element, breaching the reagent storage element and releasing the reagent, and communicating the reagent to a target.

In one aspect the step of forcing and breaching of the reagent storage element occurs in a reagent delivery column housing using centrifugal forces exerting a biasing force on the reagent storage elements.

In one aspect the step of communicating the reagent to a target includes communicating the reagent to a binding matrix.

BRIEF DESCRIPTION OF THE SEVERAL VIEWS OF THE DRAWINGS

FIG. 15A is a side of a reagent delivery apparatus according to one embodiment shown in a first state prior to reagent delivery.

FIG. 15B is a side view of the reagent delivery apparatus of FIG. 15A shown in a second state in which two reagent storage elements are pierced, according to one embodiment.

FIG. 15C is a cross-sectional view of FIGS. 15A and 15B, taken across section 15C-15C, according to one aspect.

FIG. 15D is a cross-sectional view of FIG. 15B, taken across section 15D-15D, according to one aspect.

DETAILED DESCRIPTION

Figure 1:
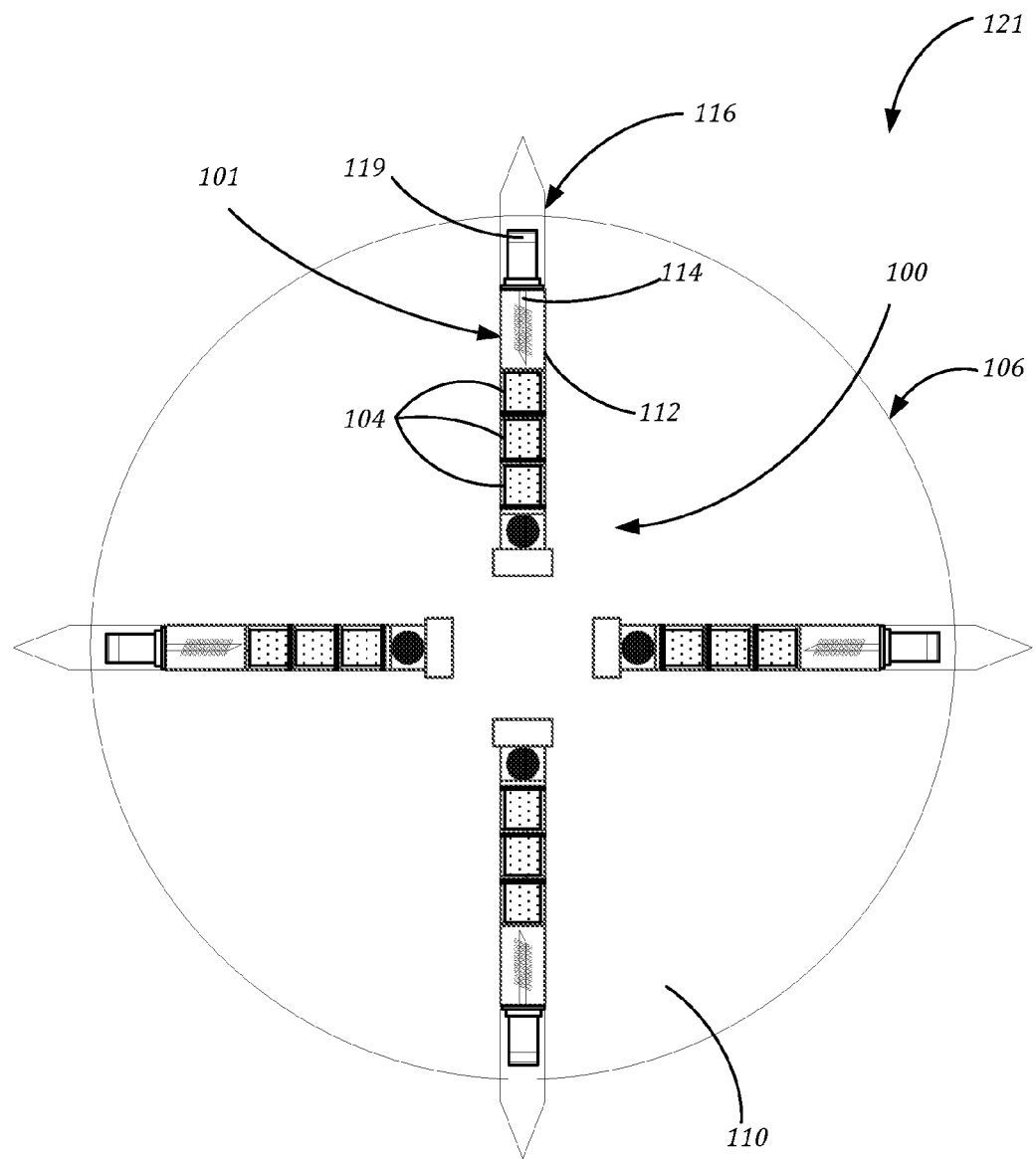
FIG. 1 is a generally plan view of a reagent delivery system according to one embodiment.

FIG. 1 illustrates a reagent delivery system 121 according to one embodiment. In one embodiment, the reagent delivery system 121 includes at least one reagent delivery device 100 configured to be coupled, positioned, or secured, with respect to an actuating source 106. In some embodiments, the actuation source 106 may include a rotational device 110, such as a centripetal or centrifugal device. For clarity of description and without any intention to limit the scope of the present disclosure, the rotational device 110 will hereinafter be referred to as the centrifugal device 110.

In one embodiment, the reagent delivery device 100 includes a reagent delivery column 101 configured to be directly or indirectly coupled to a target chamber 116. In one embodiment, the target chamber 116 can be selectively and removably coupled to the reagent delivery column 101.

Figure 2A:
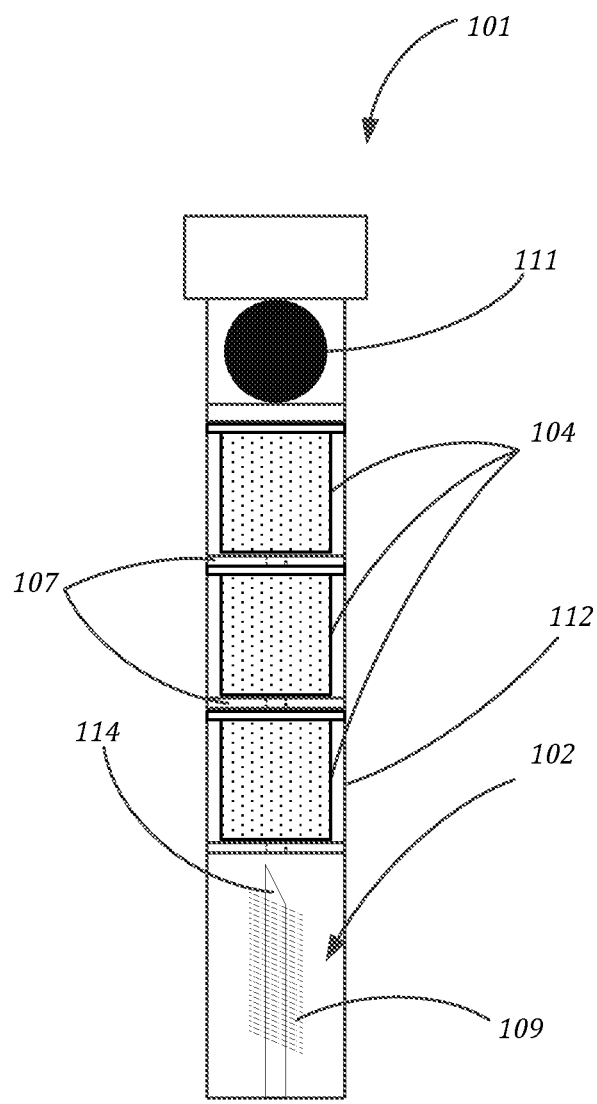
FIG. 2A is a side view of a reagent delivery column of a reagent delivery device according to one embodiment.

In one aspect, illustrated in FIG. 2A, the reagent delivery column 101 can include an egress structure, portion, or assembly 102, and at least one or a plurality of reagent storage elements 104. For clarity of description and without any intention to limit the scope of the present disclosure, the egress structure, portion, or assembly will hereinafter be referred to as the egress structure 102.

In an aspect, the reagent delivery column 101 includes a housing 112 configured to receive the reagent storage element(s) 104. In one embodiment, the reagent storage elements 104 can each include a pouch, blister, or other containing unit housing a reagent, for example a cylindrical pouch. In some aspects, each reagent storage element 104 can include a flexible pouch, which can be fabricated from any suitable material such as flexible plastic or polymeric material. In some embodiments, the reagent storage elements 104 can be prefilled with reagent fluids.

Figure 2B:
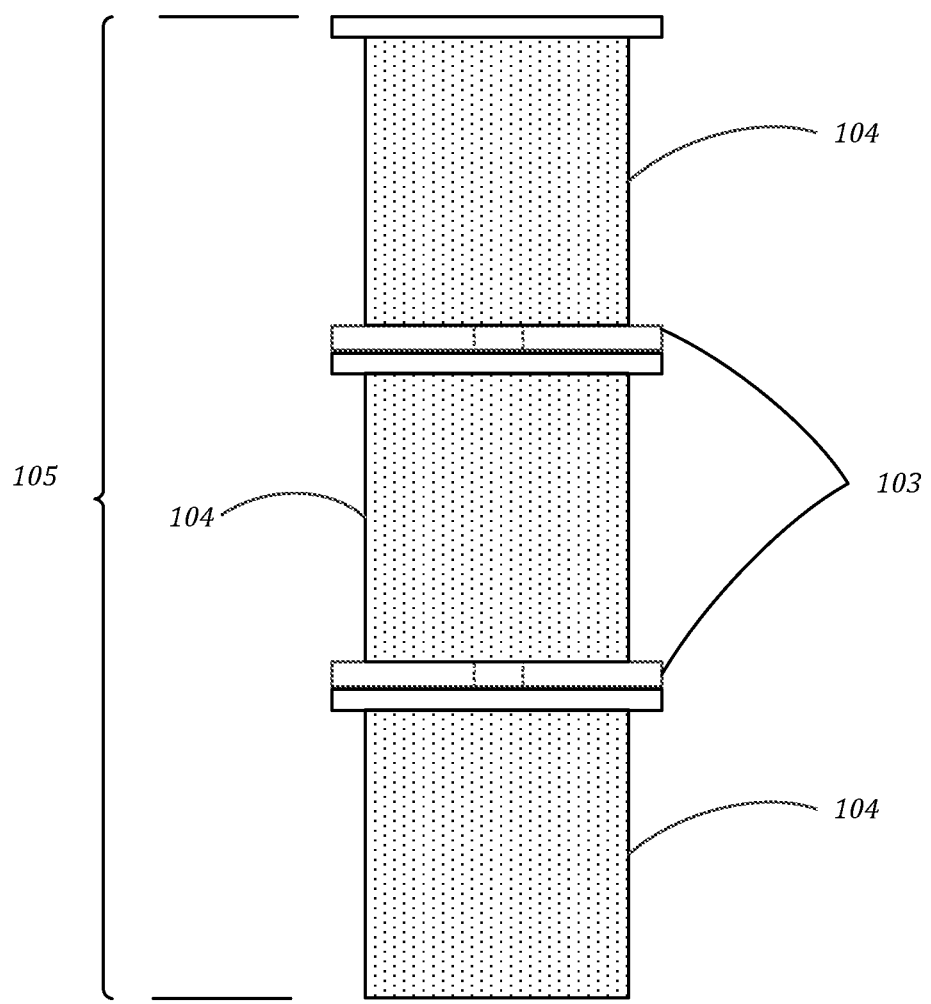
FIG. 2B is a side view of a reagent storage element stack according to one embodiment.

In one embodiment, as illustrated in FIG. 2A, the egress structure 102 includes a breaching element 114, such as a piercing or puncturing structure, for example a needle, configured to pierce, puncture, tear, or otherwise breach the reagent storage elements 104. In some embodiments, as illustrated in FIG. 2B, two or more reagent storage elements 104 can be stacked or coupled together to form a storage element stack 105, which in turn can be received in the housing 112 (FIG. 2A).

In one aspect, the reagent storage elements 104 can be permanently or removably coupled to one another. For example, the storage element stack 105 can include respective coupling members 103 positioned between respective reagent storage elements 104, coupling adjacent reagent storage elements 104. In some embodiments, the coupling members 103 can include an adhesive element, such as for example, a double-sided adhesive element. The coupling members 103 can assist maintaining the reagent storage elements 104 aligned. In some aspects, the coupling member 103 can include a void or hole toward a region where the breaching element 114 passes to avoid contact with, and/or contamination of, the breaching element 114.

As shown in FIG. 1, in one embodiment, the breaching element 114 is adapted or configured to be in fluid communication between the at least one reagent storage element 104 and the target chamber 116. The target chamber 116 can include any receptacle, chamber, flask, spin column, pouch, blister, test tube, reagent vacuole, well, or the like, and/or any combination thereof, or any suitable fluid storage or receiving element or target.

The target chamber 116 can include a column having an active element, core, and/or matrix 119, or it can include additional fluid transfer components such as distribution manifolds facilitating fluid transfer to or from the active element, core, matrix 119, or around it to a different volume in the target chamber 116. Examples of these embodiments are later described for a thorough understanding of the present disclosure without any intention to limit the scope thereof. The active element, core, matrix, and/or column can include or be made from fiberglass, sand, composites, gel, any combination thereof, and/or any other suitable material.

For clarity of description and without any intention to limit the scope of the present disclosure, some of the example embodiments that follow relate to embodiments including more than one reagent storage element 104 and where the egress structure 102 includes the breaching device 114, which is hollow. For further clarity and without any intention to limit the scope of the present disclosure the breaching device will be referred to as needle 114. It is understood and appreciated that other breaching device embodiments are contemplated to fall within the scope of the present disclosure and some non-limiting alternate embodiments thereof are described later in this disclosure.

The needle 114 in some embodiments can contain a restrictive element to control the flow of reagent or its diameter can act as such. For example, the needle 114 can include or be coupled to a nozzle acting in conjunction with the centripetal forces to achieve a desired fluid flow rate.

In one aspect, the reagent storage elements 104 can include within their respective volumes the same or distinct reagents, fluids, which may include liquid(s) and/or gas(s), suspensions, or any a combination of fluids and gases and/or any other suitable contents that may be desirable for sequential delivery to the target chamber 116. For clarity of description and without any intention to limit the scope of the present disclosure or content of the storage element, its content will be referred to as reagent.

In one embodiment, as the centrifugal device 110 operates to rotate at a threshold revolutions per minute and/or faster, movable elements in the housing 112, such as the reagent storage element(s) 104, experience a force toward the egress structure 102. For example in some aspects the movable elements in the housing 112 can experience a generally downward force in embodiments in which the reagent delivery apparatus 100 is positioned with the egress structure 102 below the movable elements.

It is understood the present disclosure contemplates within its scope other embodiments in which other mounting or positioning of a reagent delivery apparatus or portions thereof, whereby the reagent storage elements 104 may move in a direction different from, or in addition to, the downward direction in response to centripetal forces imposed by the centrifugal device 110. For example, the column 101 may be positioned with a longitudinal axis thereof at an angle with respect to a vertical axis of the centrifugal device 110.

Embodiments of the present disclosure can be configured for use with existing centrifugal devices without the need to develop custom or specialized centrifugal devices.

Furthermore, the Figures may illustrate the reagent delivery column 101 with its longitudinal axis appearing as horizontal or vertical with respect to the actuating source vertical axis for clarity of illustration; however it is understood that in various embodiments, the longitudinal axis of the reagent delivery column may be at any suitable angle with respect to the actuating source vertical axis, including an angle that is different from 90 degrees or 180 degrees, or one that is between 0 and 90 degrees.

As illustrated in FIG. 2A, some embodiments may include at least one or a plurality of spacer elements 107 respectively positioned between the reagent storage elements 104. The spacer elements 107 can contribute to promoting better translation of the storage elements 104 in housing 112 and protect the storage elements 104 from prematurely bursting. The spacer elements 107 in some aspects are hollow or include a void or opening toward a central region thereof, to facilitate easy passage over or around the needle 114. Alternatively, the spacer elements 107 can be fabricated of a material that is permeable at least in the area where the needle 114 coincides therewith.

In some embodiments, the spacer elements 107 can function to also couple the reagent storage elements 104, and serve as the coupling member 103 described above. For example, the spacer elements 107 can respectively include adhesive on opposing sides thereof which are positioned contiguous adjacent reagent storage elements 104, respectively.

In some embodiments the reagent delivery column 101 or device 100 may include a spring, foam, rubber, or other protection or biasing device 109 configured to protect the reagent storage elements 104 during transport or shipping, and facilitating a more controlled reagent delivery process during operation.

In some embodiments, the reagent delivery device 100 can include additional biasing features, such as a counter-weight element 111 positioned above or adjacent the reagent storage element 104 farthest from, or distally positioned with respect to, the breaching element 114, contributing to alignment and forcing of the reagent storage elements 104 toward the breaching element 114. Some embodiments may exclude such a biasing device. The foregoing biasing features are explained in more detail below for an example embodiment with respect to operation of an apparatus according to one aspect.

Figures 3A, 3B, 3C:
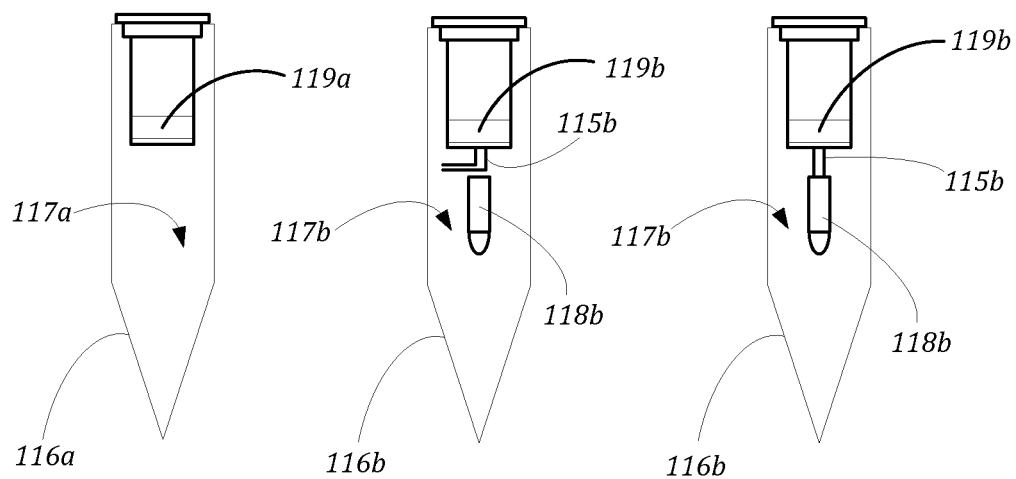
FIG. 3A is a side view of a target chamber of a reagent delivery device according to one embodiment.
FIG. 3B is a side view of a target chamber of a reagent delivery device according to another embodiment, shown in a first state in which reagent exiting a matrix in the target chamber bypasses a collection receptacle.
FIG. 3C is a side view of the target chamber of FIG. 3B, shown in a second state, according to one aspect, in which reagent exiting the matrix is communicated to the collection receptacle.

In various embodiments, the target chamber 116 can include any suitable target receiving area based on user preference and intended application. For example, FIG. 3A illustrates an example target chamber 116a. In one aspect, the target chamber 116a can include a core, column or matrix 119a configured to hold a suspension such as a suspension including an analyte and waste, and configured to bind to one of the analyte or waste, and a collection volume 117a configured to collect the other of the analyte or waste. For clarity the term "matrix" used in this context refers to a chamber that contains a matrix as differentiated from a matrix of wells later described with respect to certain embodiments like those in FIGS. 17 and 18.

FIGS. 3B and 3C illustrate another aspect in which a target chamber 116b includes a binding matrix 119b, a collection receptacle 118b, and a transfer channel or outflow selector 115b configured to communicate fluid between the binding matrix 119b, and receptacle 118b or a collection volume 117b.

In one aspect, the transfer channel 115b is configured to be movable between a first position in which the transfer channel 115b communicates fluid from the binding matrix 119b to the collection volume 117b (FIG. 3B), and a second position in which the transfer channel 115b communicates fluid from the binding matrix 119b to the receptacle 118b (FIG. 3C). In some embodiments movement of the transfer channel 115b to vary the position of its outlet between communicating fluid to the collection volume 117b and the receptacle 118b, respectively, can be controlled via automated or manual actuation, or both.

The reagent delivery column 101 (FIG. 2A) can be configured in various embodiments to be selectively coupled to any one of the target chambers 116a, 116b, described above, or any other suitable target chamber or column, such as for example a spin column similar to that described in U.S. Pat. No. 6,103,195.

Figure 4:
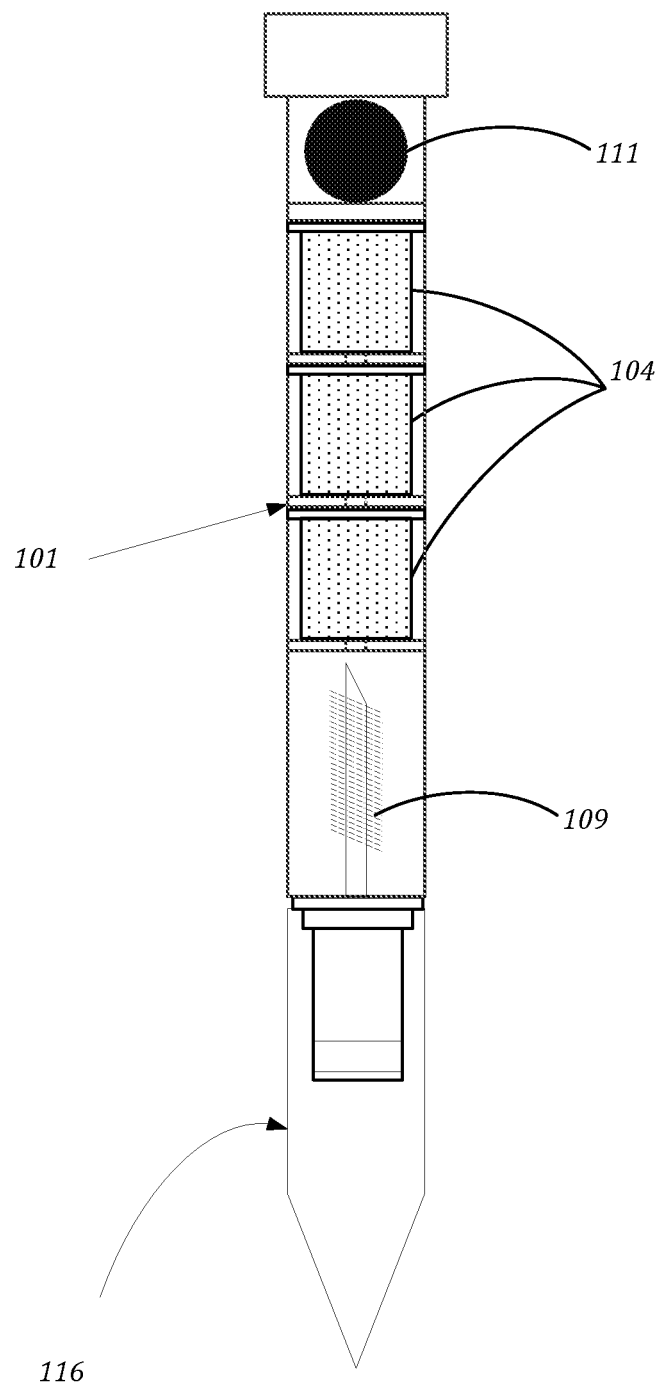
FIG. 4 is a side view of a reagent delivery device, shown in a first state prior to reagent delivery, according to one embodiment.

In the discussion that follows, the general operation of the reagent delivery column 101 according to one embodiment is described with respect to an embodiment in which the reagent delivery column 101 is coupled to the target chamber 116 as illustrated in FIG. 4, and configured to deliver reagents to the target chamber 116, without any intention to limit the scope of the type of target chamber to which a reagent delivery column according to an embodiment can deliver reagent(s).

The illustrated embodiment of FIG. 4 includes the biasing device 109 and the additional biasing element 111. For clarity of description, and without any intention to limit the scope of these biasing features and what they may include, the biasing device 109 will be referred to as spring 109 and the additional biasing element 111 will be referred to as counterweight 111.

Figures 5, 6:
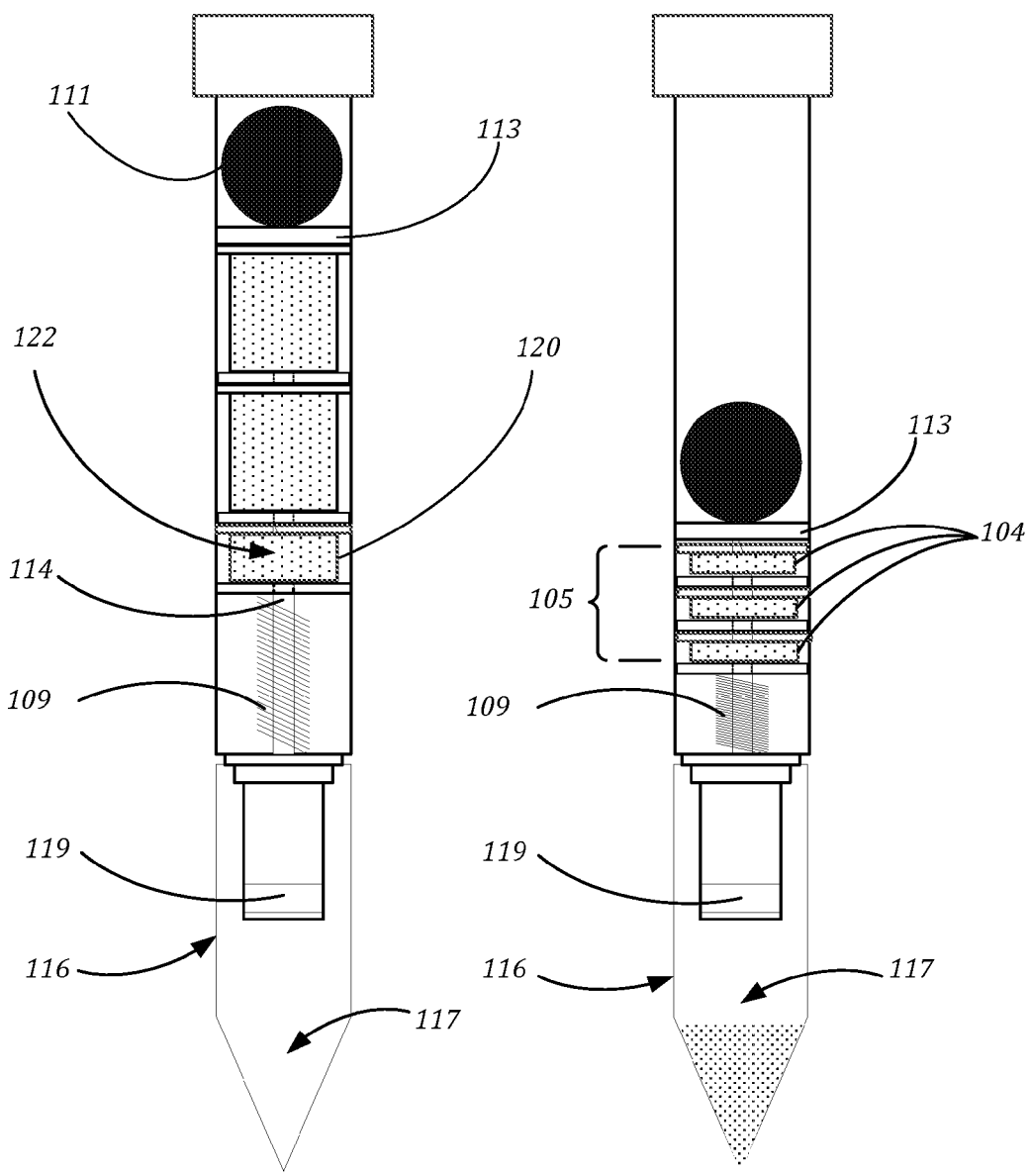
FIG. 5 is a side view of the reagent delivery device of FIG. 4, shown in a second state in which one reagent storage element is pierced, according to one aspect.
FIG. 6 is a side view of the reagent delivery device of FIG. 4, shown in a third state in which three reagent storage elements are pierced, according to one embodiment.

The biasing device 109 and counterweight 111 can include attributes that bring about desired motion characteristics for movement of the reagent storage elements 104 toward the breaching element 114. Referring to FIG. 5, in one aspect, as the centripetal forces reach a threshold level to exceed a resistance force of the spring 109 with the aid of the counterweight 111, the first reagent storage element 120 approaches and contacts the needle 114. In one embodiment as the centripetal forces further bias a first reagent storage element 120 of the plurality of reagent storage elements 104 (FIG. 4) toward the needle 114, the needle 114 pierces the first reagent storage element 120, the needle 114 becoming exposed to a first reagent 122. The first reagent 122 then flows through the hollow needle and is thereby communicated to the matrix 119 and the target chamber 116.

It is appreciated that the reagent storage elements 104 in some embodiments can move in response to centrifugal or other actuation forces, toward the needle 114 without a counterweight. This is because the reagent storage elements 104 containing reagent have a mass and centrifugal forces act on that mass biasing it to move.

In embodiments that include the counterweight 111, the counterweight 111 having a mass of its own and being positioned on a side of the storage element stack 105, advantageously assists in forcing the reagent storage elements 104 toward the needle 114. The counterweight can be designed or sized to have a particular mass. This mass along with selectively managing the forces acting the counterweight 111, for example via the centrifugal device 110, allows customizing movement characteristics of the reagent storage elements 104.

Furthermore, the spring 109 can include resistive and/or resilience characteristics and/or spring constant (or equivalent for other biasing elements) to assist in managing and customizing the movement characteristics of the reagent storage elements 104 so that they are need moving with a force and a speed beyond a threshold force and speed, respectively.

The counterweight 111 and spring 109 can respectively include weight and resistance attributes, which in combination, and when exposed to an actuation source, such as the centrifugal force of the centrifugal device 110, can bring about desired motion characteristics of the reagent storage elements 104. The lower and closer to the needle 114 a reagent storage element 104 is it experiences more force given it bears a larger mass above it. With these dynamic concepts in mind, the weight of the counterweight 111, the resistive force of the spring 109, and the speed or force of the actuation source, can be customized to achieve particular reagent storage element 104 movement speed toward the needle 114 as well as the duration of time elapsing between the times multiple storage elements 104 reach the needle 114.

In one embodiment, as illustrated in FIG. 6, as the centripetal forces continue to act on the reagent storage elements 104, the aforementioned reagent storage element consumption process continues until all reagent storage elements 104 are substantially emptied and slide down in the housing 112 circumscribing the needle 114.

In one embodiment, the apparatus 100 can include a platform 113 positioned between the counterweight 111 and the reagent storage element 104 farthest from the breaching element 114. The platform 113 can serve to transfer a force exerted by the counterweight 111 in a more evenly distributed manner, forcing the storage element stack 105 uniformly, and mitigate any damage to the reagent storage element 104. In some embodiments, the platform 113 can also serve to protect the needle 114 by preventing it from contacting the counterweight.

In one aspect, the needle 114 communicates the reagents in the reagent storage elements 104 between the respective storage elements 104 and the target chamber 116. The following non-limiting example is provided for an understanding of an example application, without any intention to limit the scope hereof to any particular application.

For example, in RNA or DNA extraction context, a suspension containing the RNA or DNA or generally nucleic acid is initially prepared and contained in an extraction column having a matrix, such as the matrix 119, and then transferred to the target chamber 116. This suspension may contain certain impurities and/or contaminants, for being processed to separate the RNA, DNA, or generally nucleic acid from the impurities.

For example, the storage element stack 105 of reagent storage elements 104 can include the same or distinct washing buffers such as 80% isopropanol, 75% ethanol, 10 mM Tris-HCl pH 7.5, 80% ethanol and/or any combination thereof or other suitable reagents, adapted or configured to remove at least some of the impurities and pass them through the matrix 119 to the collection volume 117, leaving the desired analyte bound to the binding matrix 119.

In some aspects, each reagent can perform a particular operation to the matrix 119. For example, a storage element stack 105 containing three reagent storage elements 104 could be assembled. Reagent storage element 104 proximal to the needle 114 could in some embodiments contain a Tris buffer, which when communicated to the matrix 119, it sets the PH of the matrix 119 to selectively bind RNA or DNA, while another reagent storage element 104 can contain alcohol washes to remove lipids and proteins. A third reagent storage element 104 can include a mixture of 75% ethanol and air to further wash the matrix and dry it respectively. Other suitable combinations are contemplated to be within the scope of the present disclosure, depending on the desired application and/or outcome.

Therefore, multiple and sequential suspension, solution, reagent, and/or other fluid delivery is made more efficient, expedient, and sanitary, and less labor intensive with embodiments herein by replacing manual and distinct steps with automated and less costly components, which automatically function to sequentially deliver reagents.

The speed, timing, and quantity of reagent delivery in various embodiments can be managed through controlling factors such as counterweight and biasing device design, reagent storage element volumes, centrifugal device speed and time, and introducing inert reagent storage elements such as those filled with air, between the reagent storage elements containing active reagents.

In embodiments that include the spring 109 and counterweight 111, these biasing features can counteract to aid and/or moderate in the overall force the reagent storage stack 105 experiences.

In some embodiments, a rotational velocity of the centrifugal device 110 (FIG. 1) can be set such that the spring 109 and the counterweight 111, in concert with the centrifugal forces, allow only a selected number of reagent storage elements 104 to be pierced or to pierce storage elements 104 at a particular time interval in sequence.

For example, the spring 109 can include resistance attributes such that the more the spring 109 is compressed the higher the force required to overcome its resistance. Therefore, user-selected or automated or programmed parameters as they pertain to at least one or more of centrifugal speed, counterweight 111, spring 109, and storage element 104 attributes, can be devised to control the speed and manner in which the reagent storage elements 104 approach the needle 114.

To reiterate, one of ordinary skill would appreciate the biasing device 109, referred to as a spring above for clarity of description, can in various embodiments include any suitable biasing member or material having resistance and/or resilience qualities. For example, the biasing device 109 can include at least one of a rubber, foam, spring, dampener or shock, washer spring, coil, any combination thereof, or any other suitable material, structure, and/or resistance or resilient member.

In applications where exceedingly long durations between reagent delivery are desired, an embodiment may use a centrifugal device adapted or configured to utilize a computer readable protocol to cease and restart centrifugal device operation or set the rotation speed of the centrifugal device 110 to separate the reagent storage element movement toward the needle 114 at the desired pace.

Embodiments that accommodate or include more than one reagent storage element 104 can be advantageous for sequential reagent delivery applications such as, but not limited to, Nucleic Acid extraction as described above with respect to one aspect, and/or other chemical reactions, such as protein purification, microarray hybridization, western, northern, southern blots, purifying reagents for PCR, extracting nucleic acid from gels, and/or performing buffer exchanges among others.

The reagent storage elements 104 may respectively store the same or different reagents. They can store the same reagents where it is desired for the same reagent to be delivered at intervals in the same or different quantities. In some embodiments the reagent storage element 104 volumes may vary or be the same. In some embodiments the reagent storage element(s) may respectively contain reagents which are separated by phase, via other storage element(s) containing inert or separating fluid, such as a buffer and/or air.

In some embodiments, the centripetal force can be selectively and/or automatically adjustable to control the pace at which reagents are delivered to the desired destination. For example, these parameters can be adjusted to suit protocols for certain applications such as extraction of nucleic acid, or protein using spin columns, purifying reagents for, performing buffer exchanges, or other chemical reactions.

These protocols may call for multiple reagents being added to one another or to a mixture of reagents at particular intervals and amounts. For example, in some embodiments, each reagent storage element 104 can have a particular volume. The reagent storage elements 104 can have the same or different volumes, allowing easy and expedient reagent delivery setup.

Figures 7, 8:
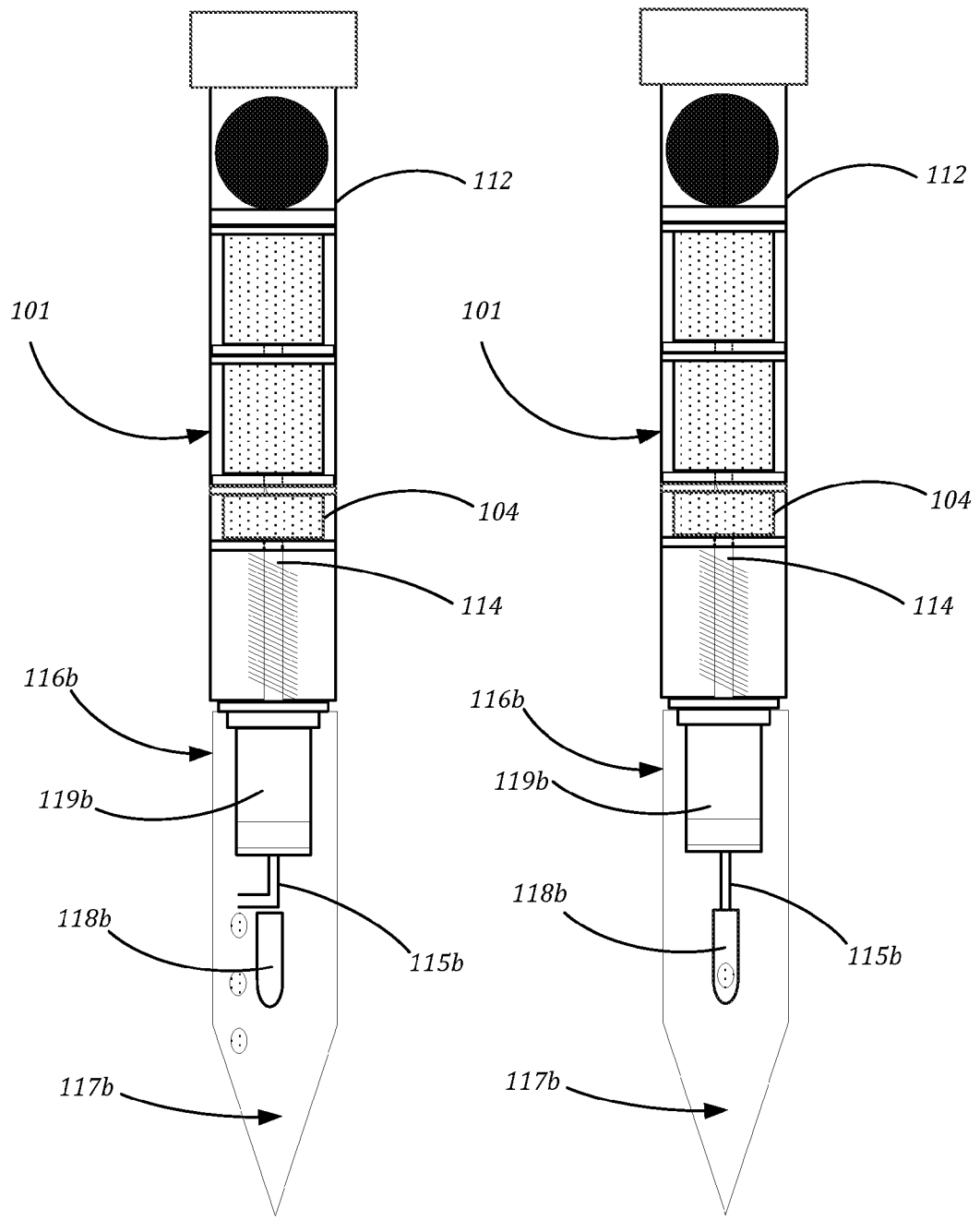
FIG. 7 is a side view of a reagent delivery device using the target chamber of FIGS. 3B and 3C, according to one embodiment, shown in a first state in which reagent exiting a matrix in the target chamber bypasses a collection receptacle.
FIG. 8 is a side view of the reagent delivery device of FIG. 7, shown in a first state, according to one aspect, in which reagent exiting the matrix is communicated to the collection receptacle.

FIGS. 7 and 8 illustrate one embodiment in which the reagent delivery column 101 is coupled to the target chamber 116b, described above and illustrated in FIGS. 3B and 3C. The reagent delivery column 101 and components therein can operate similar to what was described above to communicate reagent from the reagent storage elements 104 through the needle 114.

In the illustrated embodiment of FIGS. 7 and 8, the respective reagents can be communicated via the needle 114 through the matrix 119b, washing the desired component of the analyte suspension to the collection receptacle 118b as shown in FIG. 8, or bypassing the collection receptacle 118b, and being communicated to the collection volume 117b.

In the analyte extraction context, upon completing the wash or washes, the analyte of interest such as purified nucleic acid can be eluted from the matrix housed inside the target chamber using appropriate buffer or reagents. An eluent delivery column can be a device with the appropriate reagents and a collection tube, which can be free of degrading contaminant such as nucleic acid digestive enzyme. For example, in one embodiment an eluent delivery column can be utilized incorporating eluent storage elements similar to the reagent storage elements described above, sequentially delivering eluents to perform elution of the collected analyte. In such an embodiment, the user will replace the reagent delivery column and the target chamber with the eluent delivery column and a clean target chamber, respectively, to perform the elution.

Similar to the wash process, embodiments herein can save time and money for performing the elution in an automated and sanitary fashion.

In the illustrated embodiment of FIGS. 7 and 8, some of the reagents can selectively be delivered to the collection volume 117b and some can be delivered to the receptacle 118b. For example, in one aspect, the transfer channel 115b can be movable between a first position in which it communicates reagents from the needle 114 and reagent storage elements 104 through the matrix 119b to the collection volume 117b, bypassing the receptacle 118b, as illustrated in FIG. 7, and a second position in which it communicates remaining reagents through the matrix 119b to the receptacle 118b, as illustrated in FIG. 8.

The transfer channel 115b and/or the receptacle 118b can be rotatably or otherwise movably positioned in any suitable manner.

For example, the transfer channel 115b can be fixedly coupled to the matrix 119b, which in turn is fixedly coupled to the needle 114 or other portion of the housing 112 where rotation of the housing 112 rotates the matrix 119b and the transfer channel 115b. Alternatively, the receptacle 118b can be fixedly coupled to the target chamber 116b and rotation of the target chamber 116b rotates the receptacle 118b to position it to receive reagents from the transfer channel 115b. Other configurations are contemplated to be within the scope of the present disclosure.

Rotation of the reagent delivery column 101 and/or the target chamber 116b can be facilitated in any suitable manner. For example, the reagent delivery column 101 and/or target chamber 116b can be positioned in a receiving structure, such as a fork, receptacle, or other structure that is rotatable. In embodiments in which the actuation source 106 includes a centrifugal device, the portion of the centrifugal device receiving the reagent delivery column 101 and/or the target chamber 116b can be configured to rotate or otherwise move to alternate positioning of the transfer channel 115b outlet to fluidly communicate with the collection volume 117b and the receptacle 118b, respectively.

The rotation or movement of the transfer channel 115b can be automatic or manual. In embodiments in which the rotation is manual, the reagent delivery device 100 may include a lever or other manual actuation device to rotate the desired one of the reagent delivery column 101 or the target chamber 116b at a desired time during a reagent delivery process. In addition, or instead, the rotation actuation can be automatic and selectively programmable to initiate rotation of the transfer channel 115b at a particular time during a reagent delivery process.

For example, such embodiments will benefit from efficiency, speed, and reduced labor in contexts in which a first number of reagents are desired to be delivered to the matrix 119b then transferred to the collection volume 117b and a second number of reagents are desired to be delivered to the matrix 119b then delivered to the receptacle 118b. For example, in the nucleic acid, RNA, or DNA extraction context, the user will save time by not having to remove the reagent delivery column and replace the target chamber between the wash and elution phases.

Figure 9A:
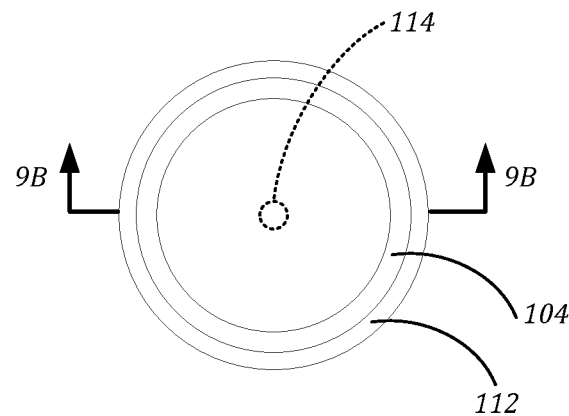
FIG. 9A is a plan view of a reagent delivery storage element and column housing according to one embodiment.
Figure 9B:
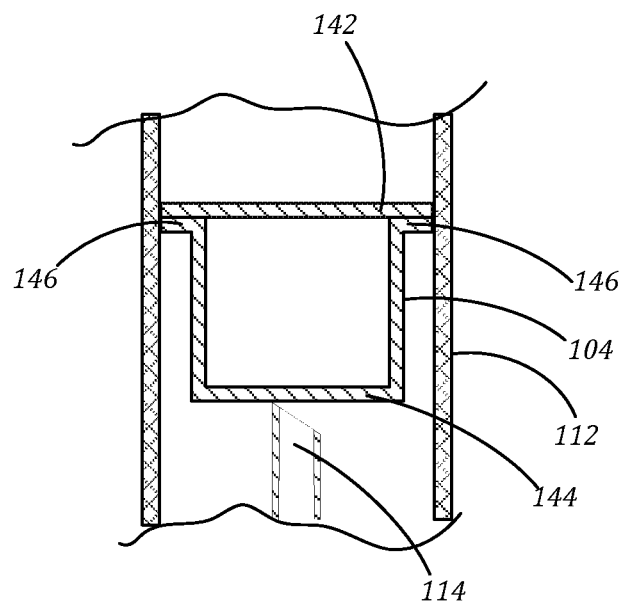
FIG. 9B is a cross-sectional view of the reagent delivery storage element and column of FIG. 9A, taken across section 9B-9B, according to one embodiment.

Referring to FIGS. 9A and 9B, in some embodiments, the housing 112 can be sized to facilitate guiding the reagent storage elements 104 in a desired travel path, for example, such that the regent storage elements 104 contact the needle 114 toward the central portion of the reagent storage elements 104. In some embodiments, the reagent storage elements 104 can include a shape that reduces friction along the housing 112 walls and promotes manufacturability.

For example, in one aspect, the reagent storage elements 104 can include a seal portion 142 and a body portion 144 having a lip or rim 146, the seal portion 142 positioned adjacent, and being coupled to, the lip 146. The overlapping portion of the seal portion 142 and lip 146 can be coupled in any suitable manner, such as heated pressed, ultrasonic welding, sewed, adhered using liquid proof adhesives, any combination thereof, and/or any other suitable coupling method.

In one aspect, as illustrated in FIG. 9B, the opposing lips or rims 146 can extend laterally beyond the remainder of the body portion 144, aligning the reagent storage element 104, at least laterally, with respect to the housing 112 and therefore, the needle 114. The lip or rim 146 maintaining a distance between the remainder of the body portion 144 and the housing 112 inner walls also reduces friction that would otherwise exist if the reagent storage element was exactly cylindrical, facilitating smoother movement in the housing 112 while remaining aligned therein.

Figure 10A:
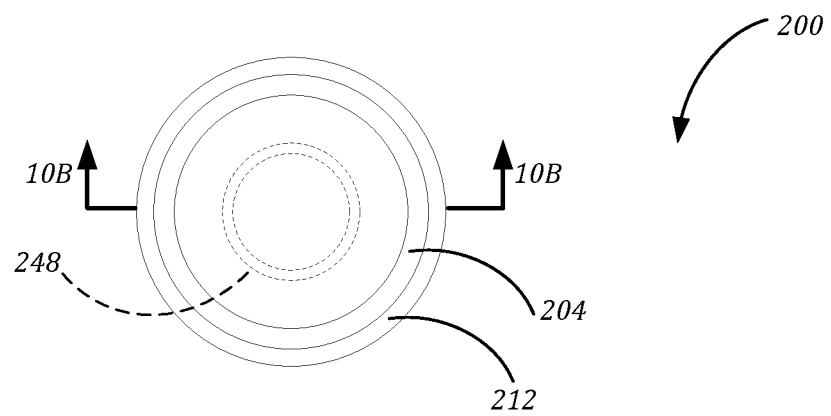
FIG. 10A is a plan view of a reagent delivery storage element and column housing according to one embodiment.
Figure 10B:
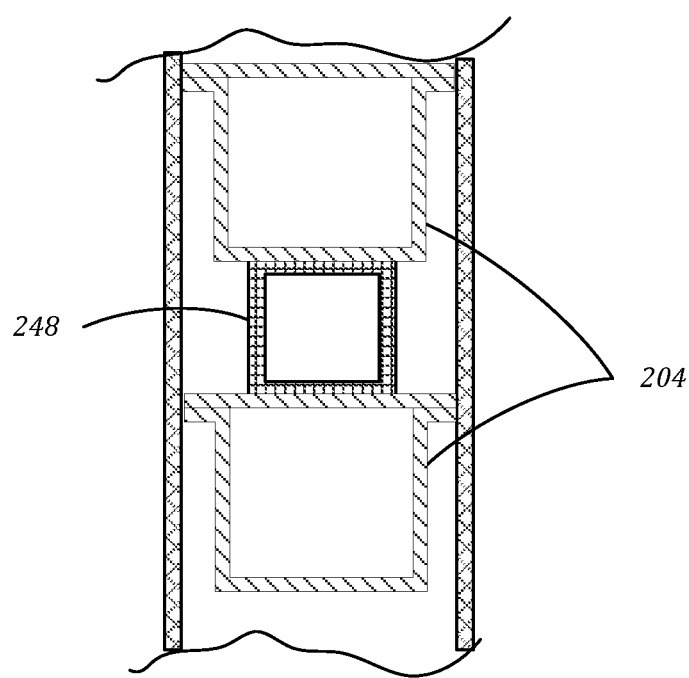
FIG. 10B is a cross-sectional view of the reagent delivery storage element and column of FIG. 10A, taken across section 10B-10B, according to one embodiment.

In another embodiment, as illustrated in FIGS. 10A and 10B, a reagent delivery device 200 can include a reagent storage element 204, which according to an aspect of the present disclosure may include features or structural elements that facilitate spacing between the reagent storage element 204 and/or that contribute to the timing or interval at which the reagents are delivered to the target chamber or spin column. For example, in one embodiment the reagent storage element 204 may include a ridge, spacer, extension, tab, or other structural element or feature 248 extending from the reagent storage element 204, and positioned between adjacent reagent storage elements 204.

Furthermore, various features of embodiments of the present disclosure can be multiplied or combined in various manners to accommodate various reagent delivery and mixing features. For example, FIG. 11 illustrates one embodiment of a reagent delivery apparatus 300 which includes more than one for example two or a plurality of reagent delivery columns 301, each including one or more reagent storage elements 304 and respective needles 314, which in turn are in fluid communication with a common target chamber such as but not limited to a spin column 316.

In such an embodiment, or various aspects thereof, the reagent storage elements 304 can be arranged identically or similarly in the respective columns 301, or alternatively, they can be arranged in a staggered or other desirable arrangement, to accommodate the proper simultaneous reagent delivery attributes suitable for the particular chemical or biochemical or other reaction or delivery as described herein or otherwise desired for a particular result.

Figure 11:
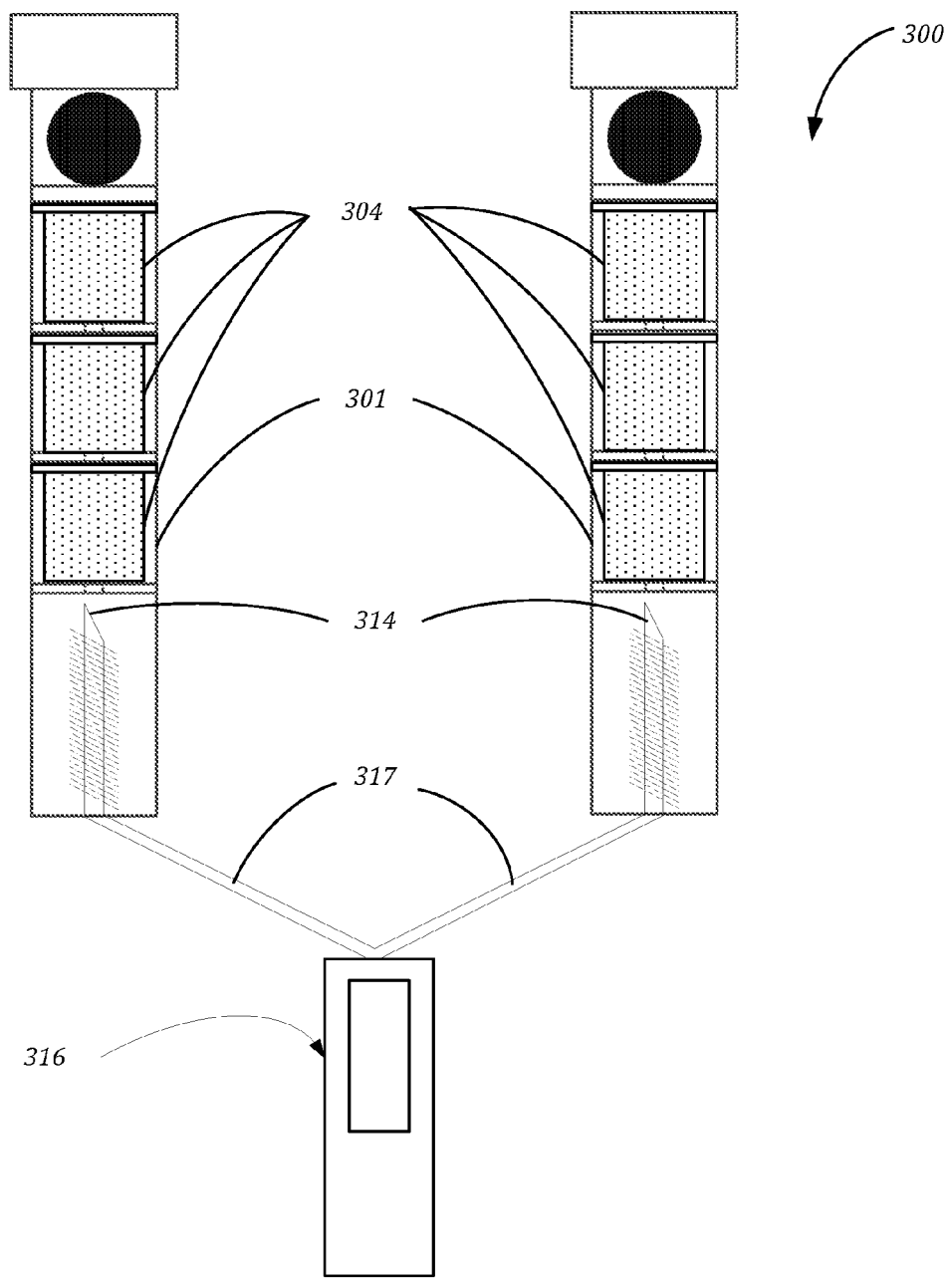
FIG. 11 is a side view of a reagent delivery apparatus according to one embodiment with more than one reagent delivery columns communicating with a target chamber.

For clarity of illustration, and without any intention to limit the scope of the present disclosure, a centrifugal device or other actuation source is not shown in FIG. 11; however, it is understood that the centrifugal device or other actuation source can be incorporated in a similar manner as described with respect other embodiments herein.

The centrifugal device in an embodiment such as that illustrated in FIG. 11 can in some aspects receive the entire apparatus 300 illustrated in FIG. 1, or it can be movable with respect to the target chamber 316 such that the target chamber 316 is in fluid communication with communication channels or other communication or delivery component or structure 317 which in turn are in communication with the needles 314.

Figure 12:
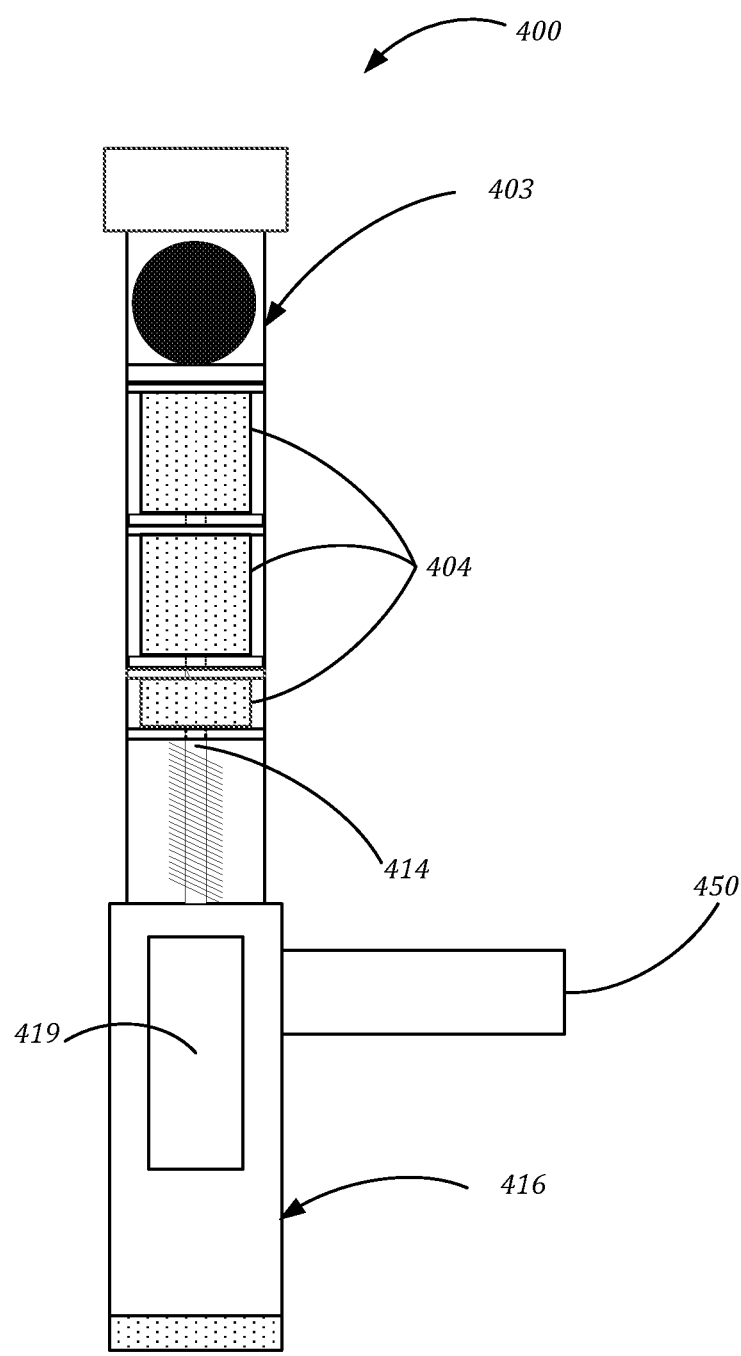
FIG. 12 is a side view of a reagent delivery apparatus according to one embodiment including a vacuum device.

In some embodiments, the force acting on reagent storage elements can originate from other or additional suitable sources. For example, FIG. 12 illustrates one embodiment of a reagent delivery apparatus 400 having a reagent delivery column housing 403, reagent storage elements 404 movably received in the housing 403, and a breaching component or needle 414 in fluid communication with a target chamber 416. In one aspect, the needle 414 is configured to communicate reagent stored in the reagent storage elements 404 upon piercing the respective reagent storage elements 404 as discussed with respect to other embodiments herein.

Instead of, or in addition to, the centrifugal device or other actuation source discussed herein, the apparatus 400 may include a vacuum device 450 coupled to the housing 403 and configured to induce a vacuum within the volume of housing 403 to affect a pull force on the reagent storage elements 404 toward the needle 414. In some embodiments, the vacuum device can be coupled to the target chamber.

Figures 13A, 13B:
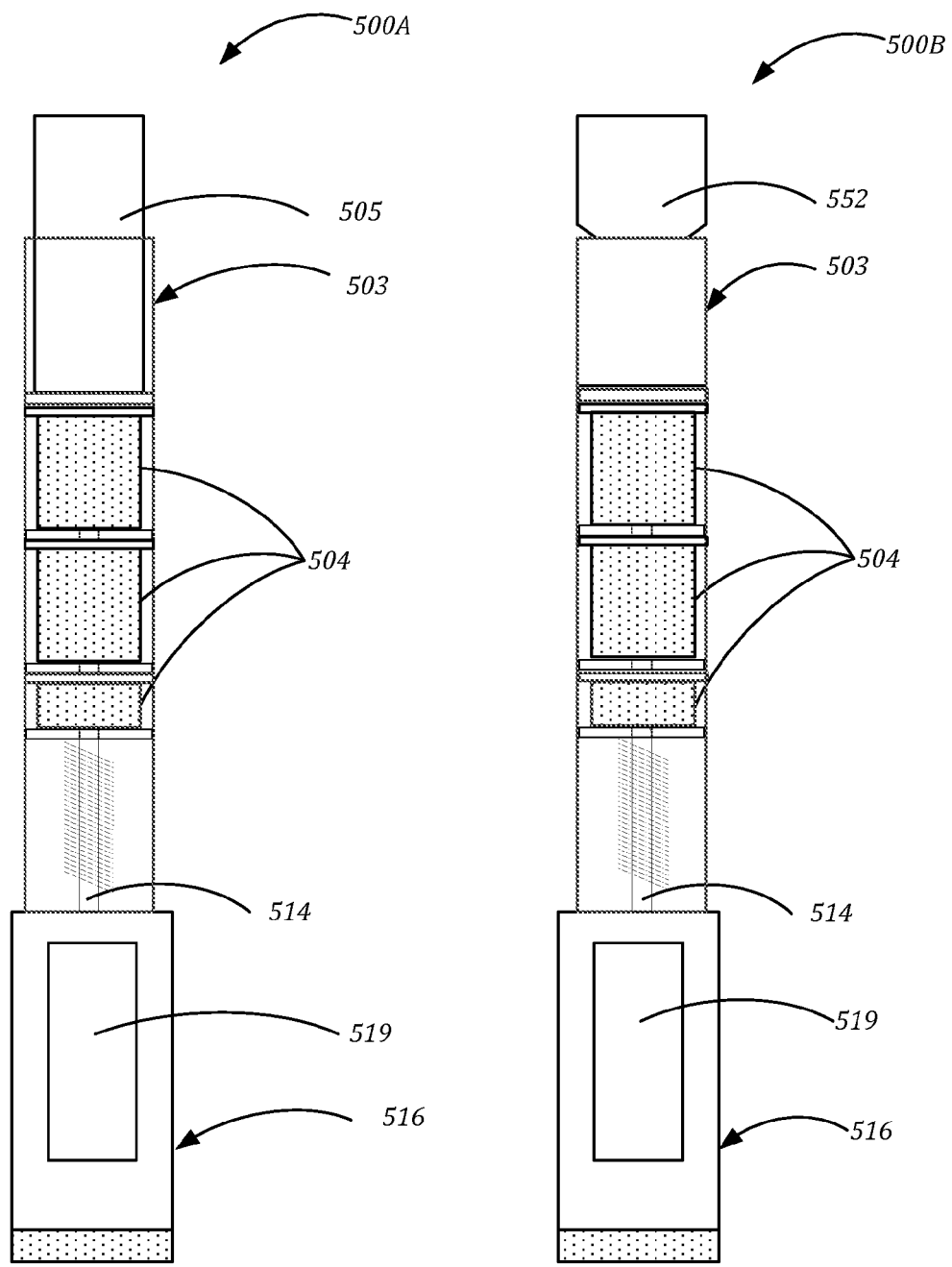
FIG. 13A is a side view of a reagent delivery apparatus according to one embodiment including a plunger.
FIG. 13B is a side view of a reagent delivery apparatus according to one embodiment including a pump device.

As a further example, FIGS. 13A and 13B illustrates embodiments of a reagent delivery apparatus 500A, 500B having a reagent delivery column housing 503, regent storage elements 504 movably received in the housing 503, and a breaching component or needle 514 in fluid communication with a target chamber 516. In one aspect, the needle 514 is configured to communicate reagent stored in the reagent storage elements 504 upon piercing the respective reagent storage elements 504 as discussed with respect to other embodiments herein.

Instead of, or in addition to, the actuation sources discussed herein, the apparatus 500A, 500B may include a thrust or push device which can bias the reagent storage elements 504 toward the needle 514, either via a physical structure such as a linear actuator, for example a plunger 505, as shown in FIG. 13A, or via exerting a fluid through hydraulic means or pneumatic means, such as an air blower or pump or a hydraulic apparatus 552, shown in FIG. 13B, operatively coupled to the housing 503 and configured to exert a fluid such as air within the volume of housing 503 to affect a push force on the reagent storage elements 504 toward the needle 514.

Figure 14:
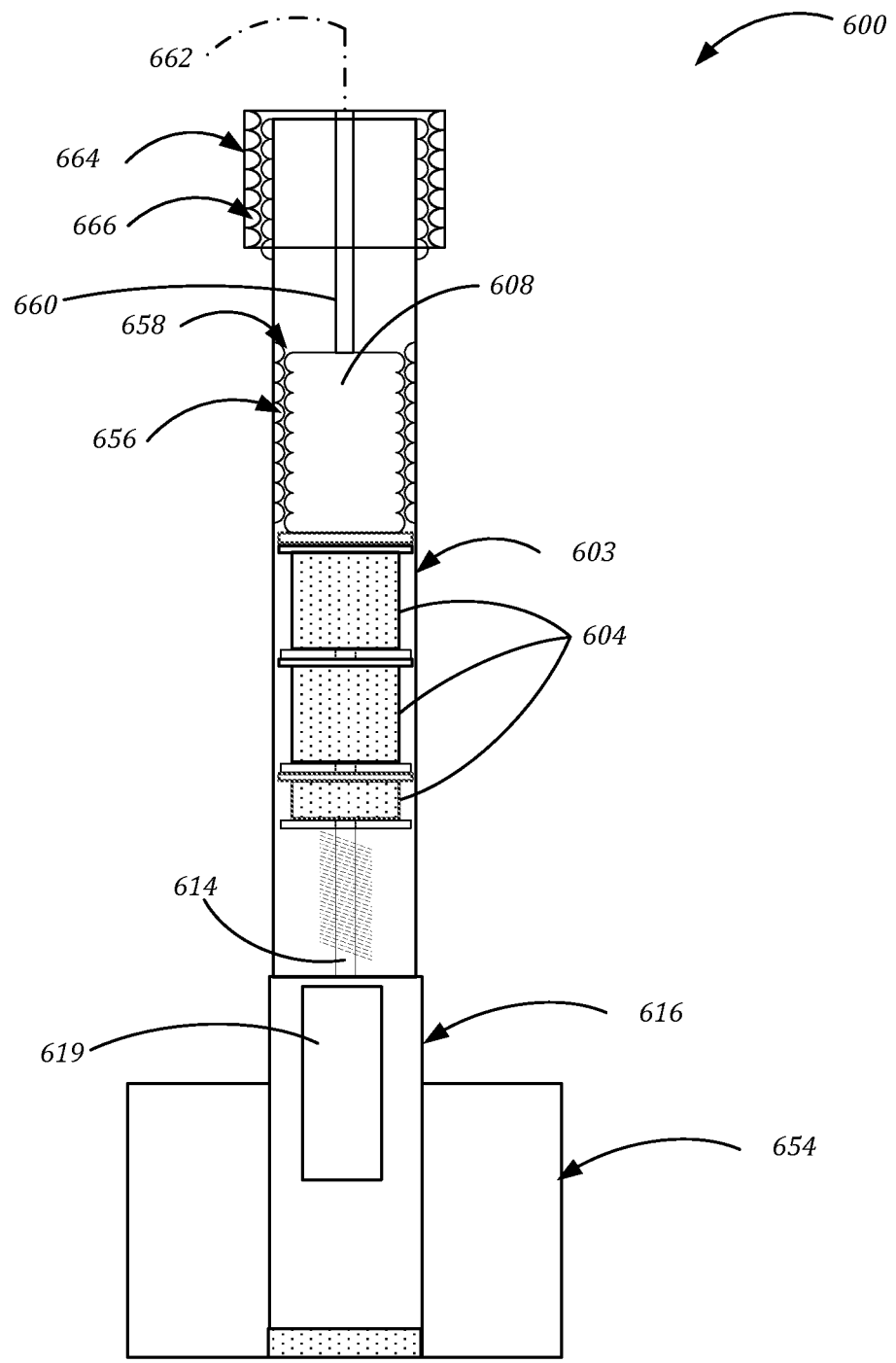
FIG. 14 is a side view of a reagent delivery apparatus according to one embodiment including a screw device.

As yet a further example, FIG. 14 illustrates one embodiment of a reagent delivery apparatus 600 having a reagent delivery column housing 603, reagent storage elements 604 movably received in the housing 603, and a breaching component or needle 614 in fluid communication with a target chamber 616. The needle 614 is configured to communicate reagent stored in the reagent storage elements 604 upon piercing the respective reagent storage elements 604 as discussed with respect to other embodiments herein.

Instead of, or in addition to, the actuation sources discussed above, the apparatus 600 may include one or more mechanical feature to exert force on the reagent storage elements 604 toward the needle 614. For example, in one aspect, the apparatus 600 may include a forcing member 608 threadedly coupled with respect to the housing 603, for example, with respect to an inner wall or surface of the housing 603. The forcing member 608 can be threadedly coupled to the housing 603 via any suitable method, such as complementary threads 656 on the forcing member 608 and the housing 603, respectively, or a lead screw or ball screw mechanism 658.

In one embodiment, the apparatus 600 can include an external threaded member 664, such as a cap. For clarity and without any intention to limit the scope of the external threaded member, the external threaded member 664 will be referred to as cap 664. In one aspect, the cap can be threadedly coupled to an outer wall of the housing 603 via a plurality of threads 666.

For clarity of illustration the threads 656, 666 are shown as wrapping partially around the forcing member 608; however, it is understood, the threads 656, 666 can in some embodiments wrap wholly around the forcing member 608 and housing 603, respectively, and that the lead screw or ball screw mechanism can include a shaft 660 extending into the forcing member 608 and being movably coupled thereto via complementary threads and balls that travel within those threads in a lead or ball screw arrangement. In such an embodiment, the shaft 660 or the forcing member 608 can be rotated via manual or automatic rotation devices to move the forcing member 608, which in turn contacts and moves the reagent storage elements 604 toward the needle 614.

In addition or instead, in some embodiments, the shaft can be fixedly coupled to the forcing member 608 and the cap 664 can be fixedly coupled to the shaft 660 to rotate therewith. In such an aspect, rotating the cap 664 rotates the forcing member 608 to move it in the housing 603.

In some embodiments, the forcing member 608 can be coupled to the housing 603 via a lead or ball screw mechanism where the forcing member 608 itself acts as the lead or ball screw shaft. In such an embodiment or in and embodiment where the forcing member 608 is threadedly coupled to the housing 603, the housing 603 can be rotated about a longitudinal axis 662 thereof, thereby the forcing member 608 translating with respect to the housing to force the reagent storage elements 604 toward the needle 614. In addition, or instead, the shaft 660 shown can be fixedly coupled to the forcing member 608 and coupled to a rotation device to rotate the forcing member 608 with respect to the housing 603 to impart movement on the forcing member 608.

It is understood not all these threaded or screw assemblies are required, and any one or more can be combined, in various embodiments. In the illustrated embodiment, the cap 664 and the housing 603 are fabricated from a transparent material, hence the internal components being visible and shown in solid lines. However, other embodiments may incorporate opaque or other transparency quality features. Transparency can facilitate visual monitoring of the device components.

Earlier it was discussed that managing time intervals between respective reagent delivery can be managed manually and/or automatically by controlling actuating source and/or introducing features between reagent storage elements; other modes of managing such intervals are contemplated to be within the scope of the present disclosure. For example, some embodiments may include movement control mechanisms in a reagent delivery column, which manage reagent delivery timing.

For example, FIGS. 15A through 15D illustrate an embodiment of a reagent delivery apparatus 700 having a reagent delivery column housing 703, reagent storage elements 704 movably received in the housing 703, and a breaching component or needle 714 configured to be in fluid communication with a target chamber. The needle 714 is configured to communicate reagent stored in the reagent storage elements 704 upon piercing the respective reagent storage elements 704 as discussed with respect to other embodiments herein.

In one aspect, the reagent delivery apparatus 700 includes at least one delivery control mechanism 730 configured or operable to selectively or automatically facilitate or prevent movement of select reagent storage elements 704 toward the needle 714. For example, in one aspect the control mechanism 730 can include a keyed element including a key feature 732, such as a receptacle, recess, depression, notch, or the like. In such aspect, the housing 703 can include a complementary key feature 734, such as a protrusion, lip, rim, ledge, or the like. The control mechanism 730 can be positioned between reagent storage elements 704 between which the delivery time interval is desired to be controlled.

For example, in the illustrated embodiment of FIGS. 15A and 15B the apparatus 700 includes first, second, and third reagent storage elements 720, 722, 724. In an application a user may desire the third storage element 724 delivered following the second storage element 722 at a time interval longer than the interval between the first and second storage elements 720, 722. In such an application, the apparatus 700 can include a control mechanism 730 between the needle 714 and the first and second storage elements 722 in a first orientation shown in FIG. 15C to allow passage of these reagent storage elements toward the needle 714, and another control mechanism 730 between the third storage elements 724 and needle 714 in a second orientation shown in FIG. 15D to prevent the third storage element from moving toward the needle 714.

Therefore, the first two storage elements 720, 722 can move and contact the needle 714 in response to an actuation source operating, while the control mechanism 730 prevents third storage element 724 from contacting the needle 714 based on the key features 732, 734 being misaligned.

In such an aspect, rotation of the control mechanism 730 to align the key features 732, 734 will facilitate movement of the control mechanism 730 and the third storage element 724. Such rotation can occur at a desired third reagent delivery time, for example manually via rotating the housing 703 or automatically via a rotation mechanism operatively coupled to the housing 703, which rotates the housing at a particular time.

Figure 16:
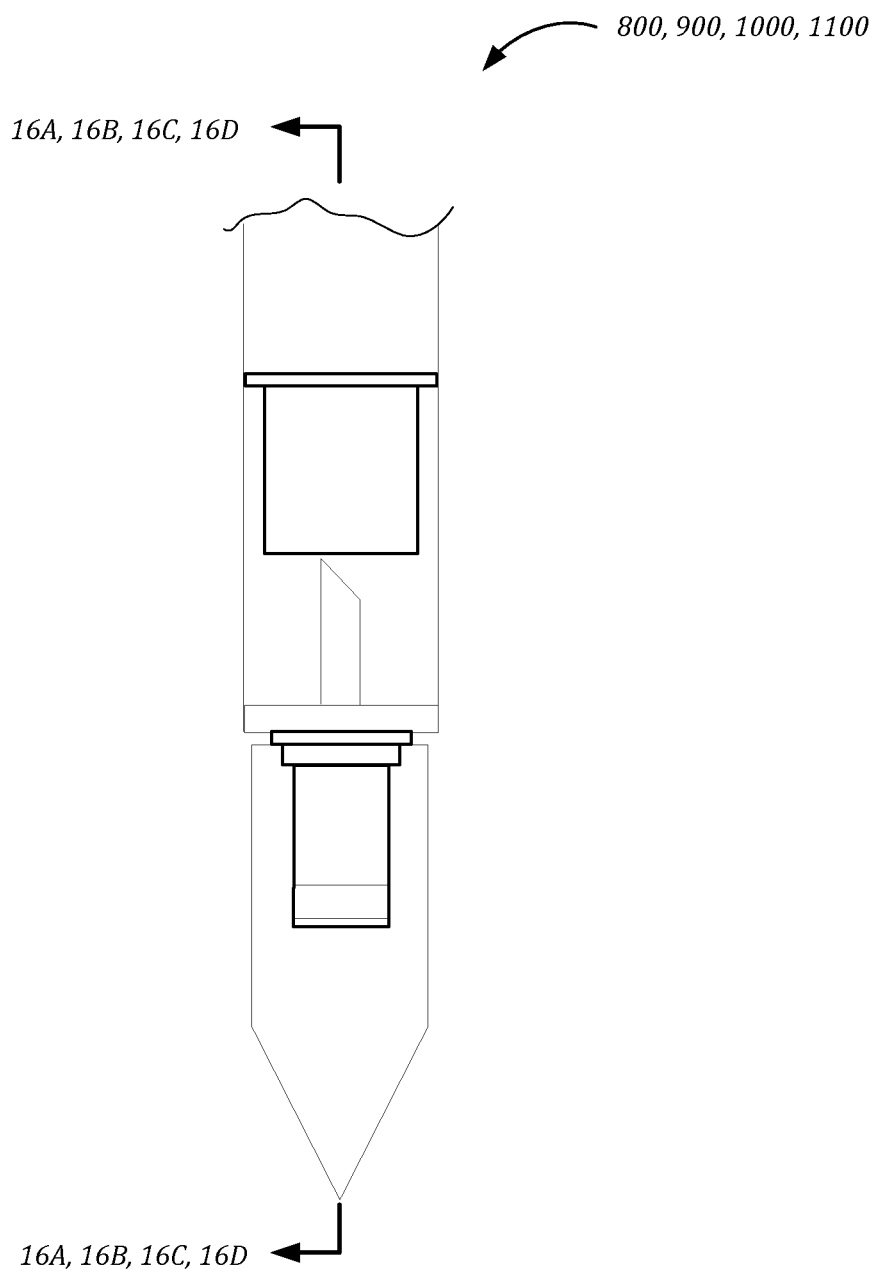
FIG. 16 is a side view of a reagent delivery apparatus configured to house internal components according to various embodiments.

Other breaching element and/or housing configurations are contemplated to be within the scope of the present disclosure, and can be used with any of the embodiments. FIG. 16 is a general side view of a reagent delivery device that can in different embodiments include various internal components. For example, FIGS. 16A through 16D illustrate cross-sections of various alternate embodiments of communicating fluid between reagent storage elements and/or apparatus housing, to a target chamber and/or matrix.

Figures 16A, 16B:
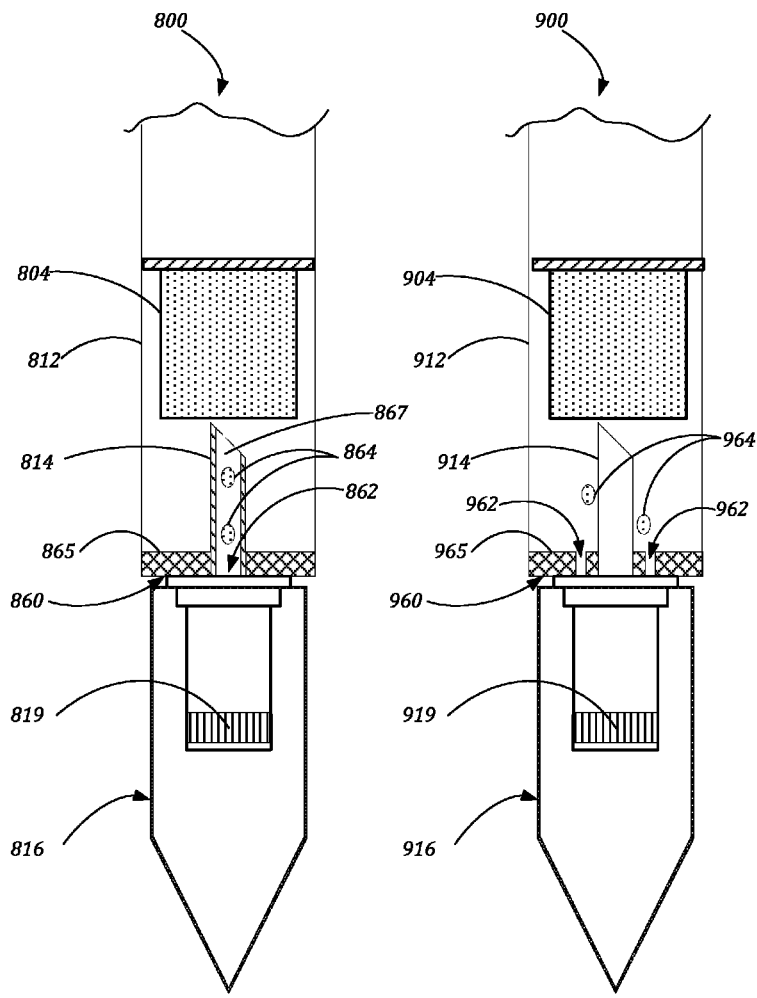
FIGS. 16A through 16D are cross-sectional views of respective reagent delivery devices according to various embodiments, taken across FIG. 16 at sections 16A, 16B, 16C, and 16D with respect to each embodiment, each including a piercing and egress configurations according to various aspects.

For example, as illustrated in FIG. 16A, a reagent delivery apparatus 800 can include a breaching element 814 and a housing 812 having a first end 860 and configured to receive one or more reagent storage elements 804. In one aspect, the housing 812 can be coupled to a target chamber 816 including a matrix 819. The breaching element 814 can include a hollow portion 867 with a sharp end, such as a needle with a beveled tip, the hollow portion 867 open to, or in fluid communication with, an orifice 862 through the first end 860. In such an embodiment, when the breaching element 814 pierces or breaches the reagent storage element 804, fluid or reagent 864 released from the reagent storage element 804, can pass through the breaching element 814 hollow portion toward the target chamber 816 or matrix 819.

The housing 812 including a portion thereof forming the first end 860 can be formed from a unitary body of material in some embodiments. In some embodiments, the housing 812 can be coupled to a plug member 865 in which opening 862 is formed, configured to secure the breaching element 814.

In another embodiment illustrated in FIG. 16B, a reagent delivery apparatus 900 can include a breaching element 914 and a housing 912 having a first end 960 and configured to receive one or more reagent storage elements 904. In one aspect, the housing 912 can be coupled to a target chamber 916 including a matrix 919. The breaching element 914 can include a solid unitary body with a sharp end such as a blade.

The first end 960 of the housing 912 can include one or more peripheral openings or orifices 962 adjacent or contiguous the breaching element 914, or spaced therefrom. In such an embodiment, when the breaching element 914 pierces or breaches the reagent storage element 904, fluid or reagent 964, can pass around the breaching element 914 through the peripheral openings or orifices 962 toward the target chamber 916 or matrix 919.

The housing 912 including a portion thereof forming the first end 960 can be formed from a unitary body of material in some embodiments. In other embodiments, the housing 912 can be coupled to a plug member 965 in which an opening is formed, configured to secure the breaching element 914. In some aspects, the openings or orifices 962 are also formed in the plug member 965.

These peripheral openings 962, in addition to allowing fluid through toward the target chamber 916, also allow air to be communicated between the housing 912 and target chamber 916, for example into and/or out of the housing 912, mitigating or preventing vacuum formation in the housing 912 and facilitating better fluid transfer toward the target chamber 916.

Figures 16C, 16D:
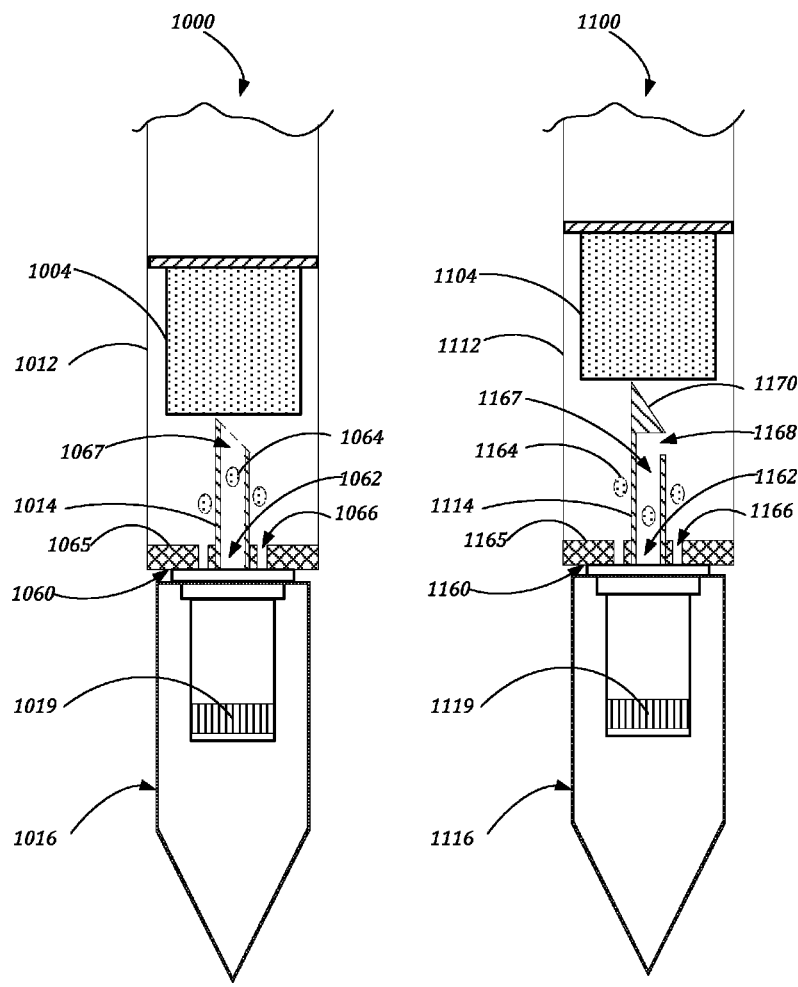

In another embodiment illustrated in FIG. 16C, a reagent delivery apparatus 1000 can include a breaching element 1014 and a housing 1012 having a first end 1060 and configured to receive one or more reagent storage elements 1004. In one aspect, the housing 1012 can be coupled to a target chamber 1016 including a matrix 1019. The breaching element 1014 can include a hollow portion 1067 with a sharp end, such as a needle, the hollow portion 1067 open to, or in fluid communication with, a central opening or orifice 1062 through the first end 1060. The first end 1060 of the housing 1012 can include one or more peripheral openings or orifices 1066 adjacent or contiguous the breaching element 1014 outer wall, or spaced therefrom.

In such an embodiment, when the breaching element 1014 pierces or breaches the reagent storage element 1004, released fluid or reagent 1064, can pass through the breaching element 1014 hollow portion 1067 and central opening or orifice 1062, as well as around the breaching element 1014 outer wall and the one or more peripheral openings or orifices 1066, toward the target chamber 1016 or matrix 1019. Similar to embodiments described above with respect to FIGS. 16A and 16B, these openings can be formed in a plug member 1065.

The peripheral openings 1066, in addition to allowing fluid through toward the target chamber 1016, also allow air to be communicated between the housing 1012 and target chamber 1016, for example into and/or out of the housing 1012, mitigating or preventing vacuum formation in the housing 1012 and facilitating better fluid transfer toward the target chamber 1016.

In another embodiment illustrated in FIG. 16D, a reagent delivery apparatus 1100 can include a breaching element 1114 and a housing 1112 having a first end 1160 and configured to receive one or more reagent storage elements 1104. In one aspect, the housing 1112 can be coupled to a target chamber 1116 including a matrix 1119. The breaching element 1114 can include a sharp end and a hollow portion 1167 having a first region in fluid communication with a side opening or orifice 1168 formed on a side of the breaching element 1114, and a second region in fluid communication with a central opening or orifice 1162 formed through the first end 1160.

In one embodiment, the breaching element 1114 includes a solid or blade portion 1170 toward the sharp end, the solid portion 1170 being adjacent the hollow portion 1167. The solid portion 1170 in the illustrated embodiment of FIG. 16D is also adjacent the opening or orifice 1168. In other embodiments, the side opening or orifice 1168 can be spaced from the solid portion 1170 along the side of the breaching element 1114 in which the orifice 1168 is formed.

The first end 1160 of the housing 1112 can in some embodiments include one or more peripheral openings or orifices 1166 adjacent or contiguous the breaching element 1114 outer wall, or spaced therefrom. The peripheral openings 1166, in addition to allowing fluid through toward the target chamber 1116, also allow air to be communicated between the housing 1112 and target chamber 1116, for example into and/or out of the housing 1112, mitigating or preventing vacuum formation in the housing 1112 and facilitating better fluid transfer toward the target chamber 1116.

In such an embodiment, when the breaching element 1114 pierces or breaches the reagent storage element 1104, released fluid or reagent 1164, can enter through the side opening or orifice 1168 and pass through the breaching element 1114 hollow portion 1167 and central opening or orifice 1162, as well as around the breaching element 1114 outer wall and second opening or orifice 1166, toward the target chamber 1116 or matrix 1119.

Similar to embodiments described above with respect to FIGS. 16A and 16B, central opening 1162 and peripheral openings 1166 can be formed in a plug member 1165.

Figure 16E:
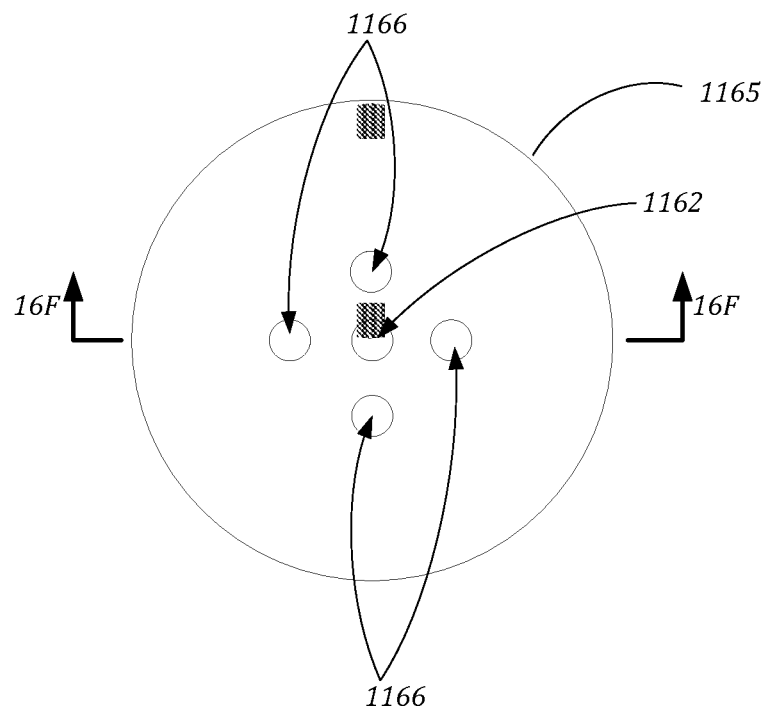
FIG. 16E is a plan view of a plug element of a reagent delivery device, according to one embodiment.
Figure 16F:
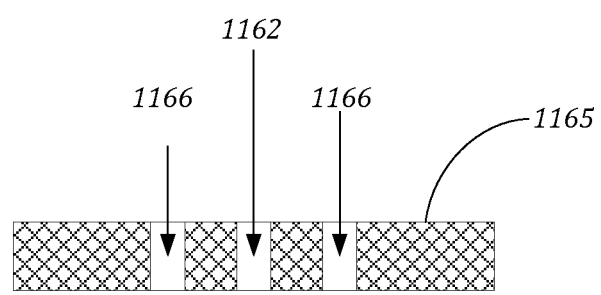
FIG. 16F is a cross-sectional view of the plug element of FIG. 16E, according to one embodiment.

FIGS. 16E and 16F illustrate one embodiment of the plug member 1165 for an understanding of an example plug member. It is understood and appreciated that other plug member embodiments may include a different shape or various opening patterns. In one embodiment, the plug member 1165 includes a central opening 1162 and four peripheral openings 1166, these openings operating as discussed above with respect to the illustrated embodiment of FIG. 16D.

Though certain embodiments and combinations have been described, other embodiments and combinations are contemplated to fall within the scope of the present disclosure. For example, some embodiments can be used with microtitre plate (spelled microtiter in the United States) or microplate or microwell plate, which is a flat plate with multiple depressions, containers, or wells used as small test tubes. Microplates typically have 6, 24, 96, 384 or even 1536 sample wells arranged in a matrix, such as a 2:3 rectangular matrix. Some microplates have even been manufactured with 3456 or even 9600 wells.

As discussed earlier the term "matrix" used in this context is different from "matrix" used with respect to the component in the target chambers described herein. Those of ordinary skill in the art appreciate the distinction.

Many of the same kits used for RNA, DNA, and Protein extraction are adapted onto these microtitre formats. Since each well can perform a single extraction, depending on the layout of the plate 48, 96, 384, etc., reactions can be performed simultaneously. For example, each plate can have a membrane at the bottom of the well, which can specifically bind to a certain target molecule. Silica gel and its derivatives can be used for such membranes. Similar to single reaction columns, well plate processing requires a set of sequential delivery of reagents to and from the plates.

An embodiment for example can serve to automate the processing of these plates similar to embodiments described, which handle single columns. For example, each well can be in fluid communication with a reagent delivery column as described with respect to embodiments herein. In some embodiments, a set of wells (e.g., 2, 3, 4, 6, 8, etc.) can be in fluid communication with one or more reagent delivery columns. In yet other embodiments, one reagent column can be configured to process an entire plate, provided sufficient distribution manifolds are incorporated. Alternatively, a number of reagent delivery columns, such as 24 of them, can serve a larger number of wells, for example, 96 wells.

Figure 17:
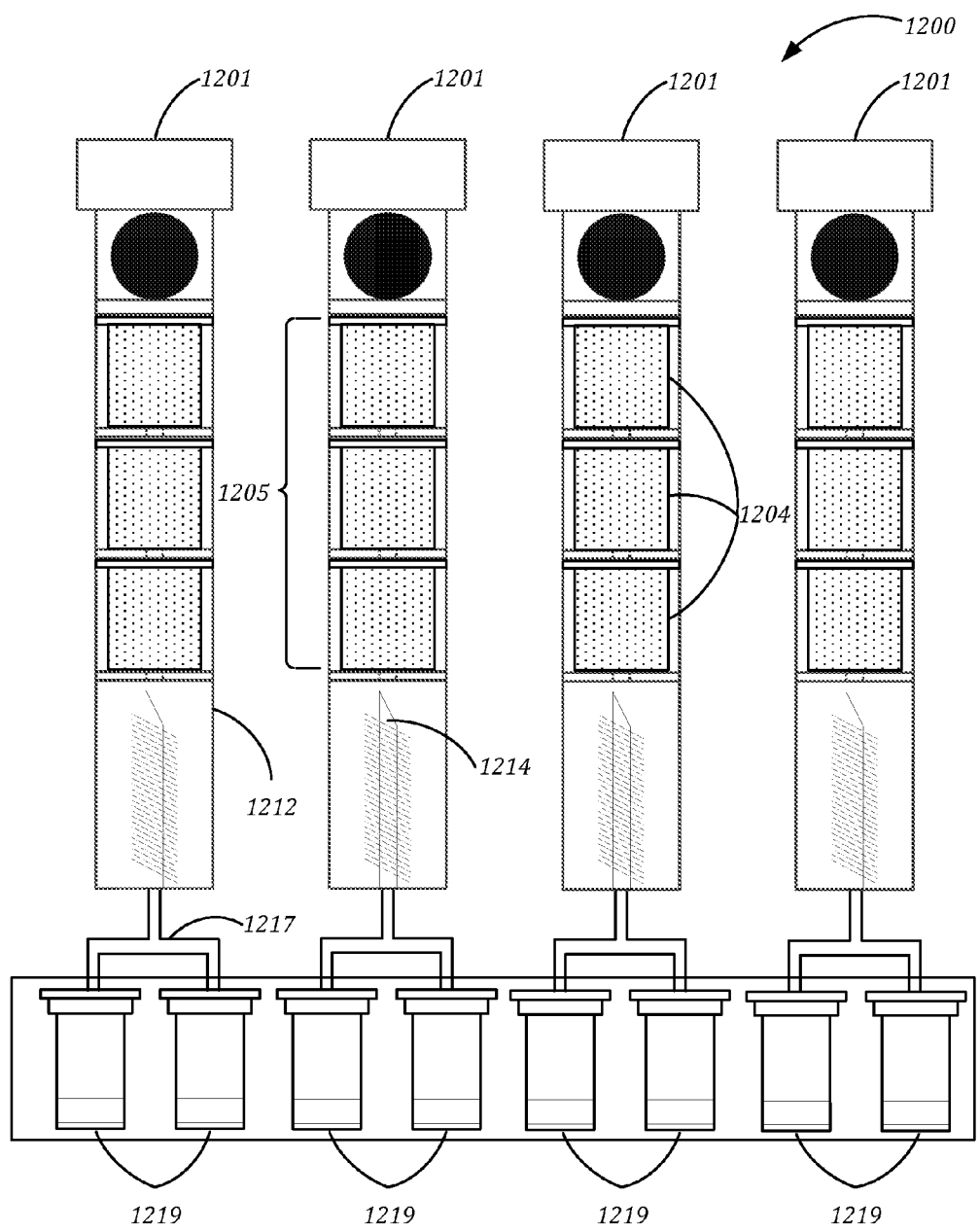
FIG. 17 is a front view of a reagent delivery system according to one embodiment including a plurality of reagent delivery devices in communication with a plurality of wells.
Figure 18:
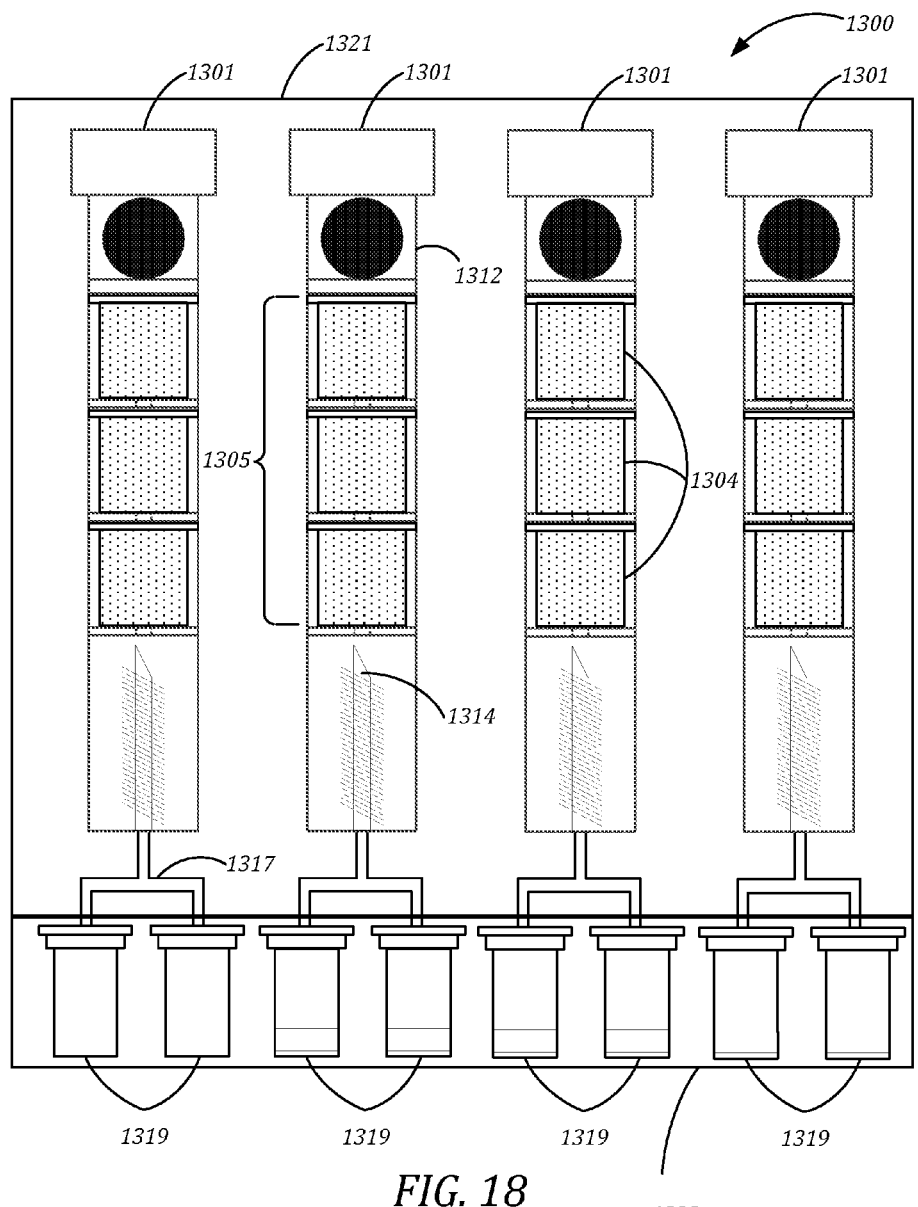
FIG. 18 is a front view of a reagent delivery system according to one embodiment including a plurality of reagent delivery devices housed in a plate in communication with a plurality of wells housed in a plate.

FIGS. 17 and 18 illustrate non-limiting examples of multiple sequential reagent delivery systems according to various embodiments, to provide a thorough understanding of using a sequential reagent delivery device along with microplates. Other multi-well sequential delivery configurations are anticipated to fall within the scope of the present disclosure.

FIG. 17 illustrates a multiple sequential reagent delivery system 1200 according to one embodiment. The system 1200 includes a plurality of reagent delivery columns 1201, each having a housing 1212 configured to receive therein one or more reagent storage elements 1204 or a storage element stack 1205, which in turn includes a plurality of storage elements 1204 stacked and/or coupled to one another.

In various embodiments, the reagent storage elements 1204 can be sequentially forced or biased toward the breaching element 1214, the breaching element 1214 piercing the reagent storage elements 1204 in a manner similar to embodiments described above and other embodiments falling within the scope of the present disclosure. For purposes of brevity and clarity, those specifics already described are omitted here without any intention to limit the scope of the present disclosure.

In one embodiment, the system 1200 includes at least one, or in the illustrated embodiment, a plurality of distribution manifolds 1217 and at least two, or in the illustrated embodiment, a plurality of wells 1219. In one embodiment, the distribution manifolds 1217, each include a first region in fluid communication with the breaching element 1214 and/or the housing 1212, and a second region in fluid communication with at least one, or in the illustrated embodiment, two wells 1219.

For example, in the illustrated embodiment of FIG. 17, each reagent delivery column 1201 is in fluid communication with two wells 1219 via corresponding distribution manifolds 1217. The wells can selectively include specific types of membranes, such as for example, RNA, DNA, Protein extraction matrix, or any other membrane depending on the desired application.

The system 1200 can be operated in any suitable manner including, without limitation, by being placed in a centrifugal device or any other biasing methods and devices described herein.

FIG. 18 illustrates a multiple sequential reagent delivery system 1300 according to one embodiment. The system 1300 includes a plurality of reagent delivery columns 1301, each having a housing 1312 configured to receive therein one or more reagent storage elements 1304 or a storage element stack 1305, which in turn includes a plurality of storage elements 1304 stacked and/or coupled to one another.

In various embodiments, the reagent storage elements 1304 can be sequentially forced or biased toward the breaching element 1314, the breaching element 1314 piercing the reagent storage elements 1304 in a manner similar to embodiments described above and other embodiments falling within the scope of the present disclosure. For purposes of brevity and clarity, those specifics already described are omitted here without any intention to limit the scope of the present disclosure.

In one embodiment, the system 1300 includes at least one, or in the illustrated embodiment, a plurality of distribution manifolds 1317 and at least two, or in the illustrated embodiment, a plurality of wells 1319. In one embodiment, the distribution manifolds 1317, each include a first region in fluid communication with the breaching element 1314 and/or the housing 1312, and a second region in fluid communication with at least one, or in the illustrated embodiment, two wells 1319.

In one embodiment, the system 1300 includes a first block or plate 1321 housing or securing the plurality of reagent delivery columns 1301, and a second block or plate 1323 housing, forming, or otherwise containing or including the plurality of wells 1319. The first and second plates 1321 and 1323 can be coupled or positioned adjacent one another such that each reagent delivery column 1301 is in fluid communication with two wells 1319 via corresponding distribution manifolds 1317. The wells 1319 can selectively include specific types of membranes, such as for example, RNA, DNA, Protein extraction matrix, or any other membrane depending on the desired application.

The system 1300 can be operated in any suitable manner including, without limitation, by being placed in a centrifugal device or any other biasing methods and devices described herein. In some embodiments, the first plate 1321 or the second plate 1323, or both, can house, form, or otherwise contain or include the distribution manifolds 1317, or portions thereof.

One of ordinary skill will appreciate other modifications can be made to embodiments described to arrive at other embodiments without departing from the scope of the present disclosure. For example, various components can be modified or replaced to accommodate specific applications. For example, if an application, experiment, or reaction it is desired that two or more reagents be mixed as they get released prior to being delivered outside a reagent delivery device housing, the reagent storage elements can be configured to allow such mixing. Such an embodiment can be advantageous to separate enzyme from solution that it is dissolved in, then mix them up when being processed.

Figures 19A, 20A:
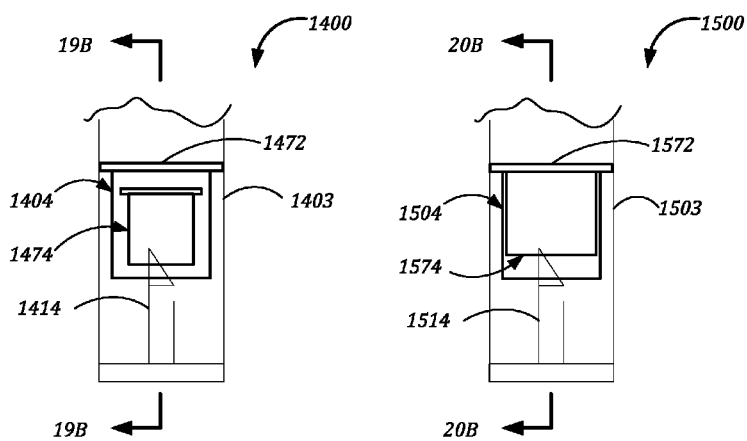
FIG. 19A is a side view of a portion of a reagent delivery device according to one embodiment showing a reagent storage element assembly according to one aspect.
FIG. 20A is a side view of a portion of a reagent delivery device according to one embodiment showing a reagent storage element assembly according to one aspect.
Figures 19B, 20B:
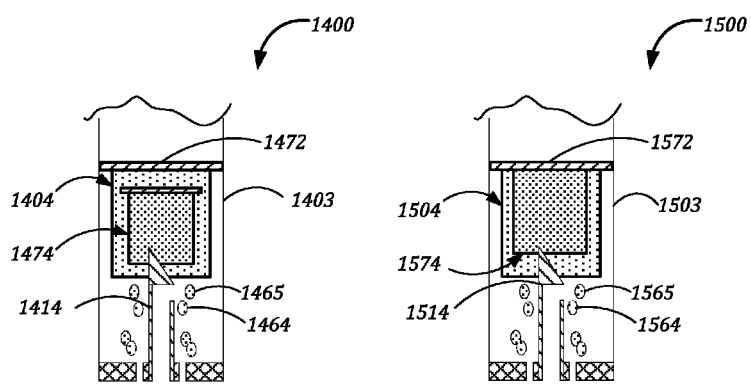
FIG. 19B is a cross-sectional view of FIG. 19A, taken across section 19B-19B, according to one embodiment.
FIG. 20B is a cross-sectional view of FIG. 20A, taken across section 20B-20B, according to one embodiment.

FIGS. 19A and 19B, illustrate a portion of a reagent delivery device 1400 according to one embodiment, including housing 1403, a breaching element 1414, and a reagent storage element assembly 1404. In one aspect the reagent storage element assembly 1404 includes a first reagent storage element 1472 nesting, housing, or containing or otherwise coupled to a second reagent storage element 1474. In one embodiment, as illustrated, when the reagent storage element assembly 1404 is actuated toward and contacts the breaching element 1414, the breaching element 1414 breaches or pierces the first and second reagent storage elements 1472, 1474, releasing first and second reagents 1464, 1465 therefrom, respectively, at about, or substantially, the same time.

Accordingly, the first and second reagents 1464, 1465 can at least partially mix in the housing 1403 prior to be delivered outside the housing 1403.

FIGS. 20A and 20B, illustrate a portion of a reagent delivery device 1500 according to another embodiment, including housing 1503, a breaching element 1514, and a reagent storage element assembly 1504. In one aspect the reagent storage element assembly 1504 includes a first reagent storage element 1572 nesting, housing, or containing, or otherwise coupled to a second reagent storage element 1574. The second reagent storage element 1574 can share a boundary with the first reagent storage element 1572, for example be sealed toward its top at a common top seal with the first reagent storage element 1572.

In one embodiment, as illustrated, when the reagent storage element assembly 1504 is actuated toward and contacts the breaching element 1514, the breaching element 1514 breaches or pierces the first and second reagent storage elements 1572, 1574, releasing first and second reagents 1564, 1565 therefrom, respectively, at about, or substantially, the same time.

Accordingly, the first and second reagents 1564, 1565 can at least partially mix in the housing 1503 prior to be delivered outside the housing 1503.

Other reagent storage element assemblies are contemplated to be within the scope of the present disclosure. For example, first and second storage elements can be coupled side by side to one another, or a reagent storage element assembly can include more than two reagent storage elements containing various or the same reagents.

Other control mechanisms are contemplated to be within the scope of the present disclosure. For example in some embodiments a biasing element such as a spring or the like can be positioned between storage elements or spacers that are between storage elements, the spring to include a particular stiffness ratio that prevents the spring from compressing when an actuation force up to a threshold force is applied thereto, and allows compression when the actuation force exceeds the threshold force. For example, in an embodiment in which the actuation force is applied by a centrifugal device, the spring does not compress when the rotation speed is at 2000 rpm; however, at rotations speeds higher than 2000 rpm, the rate and movement of the compression, and therefore, movement of the subsequent reagent storage element can be moderated.

Various described and not described components of embodiments of the present disclosure can be provided as kits for particular applications. For example, prepared reagent and/or eluent storage elements can be combined with one or more needles and/or spin columns. In some embodiments, the needle can be integrally formed with a corresponding spin column. In other embodiments, the needle can be removably and selectively coupleable with a corresponding spin column. In some embodiments, various actuation sources can be combined. Various components described herein or not described but falling with the scope of the present disclosure can be supplied in a kit in a modular fashion, allowing the user to combine elements as best suits the particular application. Furthermore, reagent storage elements can contain any suitable contents; for example in some embodiments they may contain buffers for extraction of DNA, RNA, or nucleic acid suspensions. In addition, embodiments of the present disclosure are not limited in application or reagent destination to those described, and can be used for any application where reagent delivery is desired.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLE

RNA Extraction Using One Embodiment

Reagent delivery apparatus for RNA extraction includes two parts: top and bottom. The top part includes a reagent delivery column. The bottom part includes waste and spin column compartments. The bottom part can be provided with the spin column already integrated. Alternatively users can insert an off the shelf spin column such as Qiagen™ spin columns into a receptacle fabricated into the bottom part. The reagent delivery column can contain the following example reagents in respective reagent storage elements in an order starting from bottom.

500 ul of RNAse free air.
700 ul of wash 1 or RW1 in case of Qiagen™ RNeasy™ reagents.
500 ul of RNAse free air.
500 ul of wash 2 or RPE in case of Qiagen™ RNeasy™ reagents.
500 ul of RNAse free air.
500 ul of wash 2 or RPE in case of Qiagen™ RNeasy™ reagents.
1000 ul of RNAse free dry air.

A Sample can be prepared according a protocol such as disrupting the sample according to the appropriate protocol in order to release RNA into solution. For example, the solution can be RLT lysis buffer. Then one volume of 70% ethanol can be added to the lysis buffer and mix.

Up to 700 µl of solution (RLT+EtOH+sample) can be added the to the spin column compartment of the bottom part.

The user can attach or couple the top (reagent delivery column) to the bottom part and place the assembled apparatus inside a centrifuge. The user then can close the lid and centrifuge at the recommended rate for a recommended duration such as 5 minutes or as specified by the manual instructions or other suitable protocol instructions. Following centrifuge operation, the spin column has been washed and contaminants are removed. Purified RNA can now be eluted from the spin column. To do so, the user may take the apparatus from the centrifuge, remove the top part (reagent delivery column) to expose the spin column inside the bottom part, take the spin column out of the bottom receptacle and place it inside a clean collection tube, add 30-50 µl of elution water, place it into a micro centrifuge, close the lid, and centrifuge at for example equal or greater than 8000 ref for 15 seconds or other suitable duration. The eluent then will contain the RNA and is ready for downstream applications.

This is only one non-limiting example without any intention to limit the scope of the present disclosure, and reagent delivery apparatus according to various embodiments can be used for any suitable reagent delivery application.

The invention claimed is:

1. A reagent delivery device comprising:
   at least one reagent delivery column having a housing, the housing including a housing volume;
   at least one reagent storage element configured to store reagent and movably positioned in the housing volume;
   a breaching element coupled to the housing and configured to breach the at least one reagent storage element, at least one of the breaching element and the housing configured to communicate reagent from at least one of the housing volume and the reagent storage element, to an external volume located externally with respect to the housing volume; and
   a centrifugal device configured to rotate, the reagent delivery column selectively positionable in the centrifugal device, rotation of the centrifugal device producing centrifugal forces moving the at least one reagent element toward the breaching element when in operation, wherein each reagent storage element includes a body portion having a width and a length, and a seal portion, the seal portion extending laterally beyond the width of the body portion, the seal portion contacting the housing, the body portion being spaced from the housing.

2. The reagent delivery device of claim 1 wherein each reagent storage element has an outer surface and the housing has an inner surface, the outer surface of each reagent storage element having a first portion and a second portion, the first portion being contiguous the inner surface of the housing and the second portion being spaced from the inner surface of the housing.

3. The reagent delivery device of claim 2 wherein the first portion of the outer surface of each storage element has a surface area smaller than a surface area of the second portion of the outer surface of that storage element.

4. The reagent delivery device of claim 1 wherein the seal portion of the reagent storage element is of the reagent storage element is smaller than the length of the body portion.

5. The reagent delivery device of claim 1, further comprising:
   at least one spacer element, the at least one reagent storage element including at least two reagent storage elements, each spacer element positioned between respective adjacent reagent storage elements, the spacer elements each carrying an adhesive layer on opposing sides thereof and coupling the respective adjacent reagent storage elements, the spacer elements collectively coupling the plurality of reagent storage elements to form an integral reagent storage element stack and align their positions with respect to each other and the reagent delivery column.

6. The reagent delivery device of claim 1, further comprising:
   a control system configured to moderate movement of the reagent storage element toward the breaching element wherein the control element includes a keyed spacer having a recessed key feature, the keyed spacer configured to cease movement of subsequent reagent storage elements upon being blocked by a tabbed key feature coupled to the housing, and allowing movement thereof upon rotation of the keyed spacer to align the recessed and tabbed key features such that the tabbed key feature passes through the recessed key feature.

7. The reagent delivery device of claim 1, further comprising:
   a weight positioned on a first side of the reagent storage elements distal with respect to the breaching element and a biasing device on a second side of the reagent elements proximal with respect to the breaching element, wherein the centrifugal forces impart motion to the weight resulting in a momentum of the weight forcing the reagent storage elements toward the breaching element, the biasing device having resistance properties to moderate movement of the reagent storage element toward the breaching element.

8. The reagent delivery device of claim 1 wherein the breaching element includes a blade leading edge coupled to a hollow stem including a side having at least one orifice therethrough.

9. The reagent delivery device of claim 1, further comprising:
   a plug element coupled to the housing and securing the breaching element, the plug element including at least one peripheral opening therethrough, the peripheral opening laterally spaced from the breaching element.

10. The reagent delivery device of claim 1 wherein the at least one reagent storage element includes an assembly including a first reagent storage element and at least a second reagent storage element coupled to the first reagent storage element in adjacent proximity such that the breaching element breaches the first and second reagent storage elements substantially simultaneously, reagent contained in the first and second reagent storage elements mixing in the housing volume.

11. A reagent delivery device comprising:
   at least one reagent delivery column having a housing, the housing including a housing volume;
   at least one reagent storage element configured to store reagent and movably positioned in the housing volume;
   a breaching element coupled to the housing and configured to breach the at least one reagent storage element, at least one of the breaching element and the housing configured to communicate reagent from at least one of the housing volume and the reagent storage element, to an external volume located externally with respect to the housing volume;
   a centrifugal device configured to rotate, the reagent delivery column selectively positionable in the centrifugal device, rotation of the centrifugal device producing centrifugal forces moving the at least one reagent element toward the breaching element when in operation; and
   a target chamber coupled to the reagent delivery column and forming the external volume in fluid communication with at least one of the breaching element and the housing volume, the target chamber having an active element column, a receptacle, and a collection volume, the active element column configured to be selectively in fluid communication between the receptacle and collection volume, respectively.

12. The reagent delivery device of claim 11, further comprising:
a transfer channel in fluid communication with the active element column and selectively movably coupled with respect to the target chamber, the transfer channel selectively movable between a first position in which it communicates fluid between the active element column and the collection volume, and a second position in which it communicates fluid between the active element column and the receptacle.

13. The reagent delivery device of claim 11 wherein the reagent delivery column is removably coupled to the target chamber.

\* \* \* \* \*